(12) United States Patent
Wang et al.

(10) Patent No.: US 8,974,496 B2
(45) Date of Patent: Mar. 10, 2015

(54) INTERSPINOUS IMPLANT, TOOLS AND METHODS OF IMPLANTING

(76) Inventors: Jeffrey Chun Wang, Sherman Oaks, CA (US); Thomas Neil Scioscia, Midlothian, VA (US); Adrian Slattery, Rocky River, OH (US); Alan W. Cannon, Sunnyvale, CA (US)

(*) Notice: Subject to any disclaimer, the term of this patent is extended or adjusted under 35 U.S.C. 154(b) by 1937 days.

(21) Appl. No.: 11/897,282

(22) Filed: Aug. 30, 2007

(65) Prior Publication Data

US 2009/0062918 A1 Mar. 5, 2009

(51) Int. Cl.
*A61B 17/70* (2006.01)
*A61B 17/88* (2006.01)
*A61B 17/02* (2006.01)

(52) U.S. Cl.
CPC ......... *A61B 17/7062* (2013.01); *A61B 17/8805* (2013.01); *A61B 2017/0256* (2013.01)
USPC .......................................................... 606/248

(58) Field of Classification Search
USPC .................................. 606/248, 258, 259, 249
See application file for complete search history.

(56) References Cited

U.S. PATENT DOCUMENTS

| | | | |
|---|---|---|---|
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,404,967 A * | 9/1983 | Bacal et al. | 606/276 |
| 4,448,191 A | 5/1984 | Rodnyansky et al. | |
| 4,479,491 A | 10/1984 | Martin | |
| 4,501,269 A | 2/1985 | Babby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,604,995 A | 8/1986 | Stephens et al. | |

(Continued)

FOREIGN PATENT DOCUMENTS

| | | |
|---|---|---|
| EP | 1 138 268 A1 | 10/2001 |
| FR | 2 681 525 A1 | 3/1993 |

(Continued)

OTHER PUBLICATIONS

Senegas., Mechanical Supplementation by Non-Rigid Fixation in Degenerative Intervertebral Lumber Segments: The Wallis System. ( Suppl.2): S164-S169, 2002.

*Primary Examiner* — Christian Sevilla
(74) *Attorney, Agent, or Firm* — Law Office of Alan W. Cannon

(57) ABSTRACT

Devices, tools and methods for minimally invasive implantation and distraction between spinous processes for treatment of spinous disorders. An interspinous implant device for distracting at least one pair of adjacent spinous processes includes a main body including a shaft having a longitudinal axis; and first and second arms extending transversely from the main body, wherein at least one of the first and second arms is slidably mounted with respect to the shaft. The arms are configured and dimensioned to extend laterally from both sides of the spinous processes when implanted therebetween and to be inserted between the spinous processes laterally from a single side thereof. The arms are variably positionable between a closed configuration, to facilitate insertion of the arms between the adjacent spinous processes, and an open configuration, in which the arms are separated from one another.

20 Claims, 14 Drawing Sheets

(56) References Cited

U.S. PATENT DOCUMENTS

| | | |
|---|---|---|
| 4,611,582 A | 9/1986 | Duff |
| 4,636,217 A | 1/1987 | Ogilvie et al. |
| 4,643,178 A | 2/1987 | Nastari et al. |
| 4,653,481 A | 3/1987 | Howland et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,863,476 A | 9/1989 | Shepperd |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,030,220 A | 7/1991 | Howland |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,116,334 A | 5/1992 | Cozad et al. |
| 5,123,926 A | 6/1992 | Pisharodi |
| 5,129,899 A | 7/1992 | Small et al. |
| 5,147,359 A | 9/1992 | Cozad et al. |
| 5,154,718 A | 10/1992 | Cozad et al. |
| 5,167,662 A | 12/1992 | Hayes et al. |
| 5,180,381 A | 1/1993 | Aust et al. |
| 5,192,327 A | 3/1993 | Brantigan |
| 5,201,734 A | 4/1993 | Cozad et al. |
| 5,236,456 A * | 8/1993 | O'Leary et al. ............ 623/23.63 |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,330,473 A | 7/1994 | Howland |
| 5,352,225 A | 10/1994 | Yuan et al. |
| 5,387,213 A | 2/1995 | Breard et al. |
| 5,390,683 A | 2/1995 | Pisharodi |
| 5,393,036 A * | 2/1995 | Sheridan ...................... 254/100 |
| 5,395,372 A | 3/1995 | Holt et al. |
| 5,415,661 A | 5/1995 | Holmes |
| 5,443,514 A | 8/1995 | Steffee |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,507,813 A * | 4/1996 | Dowd et al. ................ 623/23.63 |
| 5,514,180 A | 5/1996 | Heggeness et al. |
| 5,534,028 A | 7/1996 | Bao et al. |
| 5,534,029 A | 7/1996 | Shima |
| 5,540,689 A | 7/1996 | Sanders et al. |
| 5,549,607 A | 8/1996 | Olson et al. |
| 5,549,679 A | 8/1996 | Kuslich |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,824,098 A | 10/1998 | Stein |
| 5,836,948 A | 11/1998 | Zucherman et al. |
| 5,860,977 A | 1/1999 | Zucherman et al. |
| 5,865,846 A | 2/1999 | Bryan et al. |
| 5,876,404 A | 3/1999 | Zucherman et al. |
| 5,885,299 A | 3/1999 | Winslow et al. |
| 5,888,224 A | 3/1999 | Beckers et al. |
| 5,888,226 A | 3/1999 | Rogozinski |
| 5,895,387 A * | 4/1999 | Guerrero et al. .............. 606/71 |
| 5,928,232 A | 7/1999 | Howland et al. |
| 5,976,186 A | 11/1999 | Bao et al. |
| 6,001,130 A | 12/1999 | Bryan et al. |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,155 A | 6/2000 | Michelson |
| 6,090,112 A | 7/2000 | Zucherman et al. |
| 6,113,639 A | 9/2000 | Ray et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,156,067 A | 12/2000 | Bryan et al. |
| 6,183,471 B1 | 2/2001 | Zucherman et al. |
| 6,190,387 B1 | 2/2001 | Zucherman et al. |
| 6,234,705 B1 | 5/2001 | Troxell |
| 6,235,030 B1 | 5/2001 | Zucherman et al. |
| 6,238,397 B1 | 5/2001 | Zucherman et al. |
| 6,251,140 B1 | 6/2001 | Marino et al. |
| 6,280,444 B1 | 8/2001 | Zucherman et al. |
| 6,290,724 B1 | 9/2001 | Marino |
| 6,332,883 B1 | 12/2001 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,116 B1 * | 12/2002 | Knapp .......................... 600/232 |
| 6,500,178 B2 | 12/2002 | Zucherman et al. |
| 6,514,256 B2 | 2/2003 | Zucherman et al. |
| 6,652,527 B2 * | 11/2003 | Zucherman et al. .......... 606/249 |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,761,720 B1 | 7/2004 | Senegas |
| 6,902,566 B2 | 6/2005 | Zucherman et al. |
| 6,921,403 B2 | 7/2005 | Cragg et al. |
| 7,014,633 B2 | 3/2006 | Cragg |
| 7,029,473 B2 | 4/2006 | Zucherman et al. |
| 8,097,021 B1 * | 1/2012 | Kornel ........................ 606/248 |
| 2001/0020170 A1 | 9/2001 | Zucherman et al. |
| 2002/0091446 A1 | 7/2002 | Zucherman et al. |
| 2002/0116000 A1 | 8/2002 | Zucherman et al. |
| 2003/0065330 A1 | 4/2003 | Zucherman et al. |
| 2003/0139814 A1 | 7/2003 | Bryan |
| 2003/0158557 A1 | 8/2003 | Cragg et al. |
| 2003/0204189 A1 | 10/2003 | Cragg |
| 2004/0153071 A1 | 8/2004 | Zucherman et al. |
| 2004/0167520 A1 | 8/2004 | Zucherman et al. |
| 2004/0181282 A1 | 9/2004 | Zucherman et al. |
| 2004/0220568 A1 | 11/2004 | Zucherman et al. |
| 2004/0220582 A1* | 11/2004 | Keller ............................ 606/99 |
| 2004/0220668 A1 | 11/2004 | Eisermann et al. |
| 2004/0236331 A1 | 11/2004 | Michelson |
| 2004/0249379 A1 | 12/2004 | Winslow et al. |
| 2005/0010293 A1 | 1/2005 | Zucherman et al. |
| 2005/0010298 A1 | 1/2005 | Zucherman et al. |
| 2005/0033291 A1 | 2/2005 | Ebara |
| 2005/0075634 A1 | 4/2005 | Zucherman et al. |
| 2005/0125065 A1 | 6/2005 | Zucherman et al. |
| 2005/0143738 A1 | 6/2005 | Zucherman et al. |
| 2005/0165398 A1 | 7/2005 | Reiley |
| 2005/0203512 A1 | 9/2005 | Hawkins et al. |
| 2005/0203529 A1 | 9/2005 | Boehm, Jr. |
| 2005/0203624 A1 | 9/2005 | Serhan et al. |

(56) References Cited

U.S. PATENT DOCUMENTS

| | | |
|---|---|---|
| 2005/0216017 A1 | 9/2005 | Fielding et al. |
| 2005/0228383 A1 | 10/2005 | Zucherman et al. |
| 2005/0228384 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2006/0004447 A1 | 1/2006 | Mastrorio |
| 2006/0015181 A1 | 1/2006 | Elberg |
| 2006/0036246 A1 | 2/2006 | Carl et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0079898 A1 | 4/2006 | Ainsworth et al. |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084992 A1 | 4/2006 | Michelson |
| 2006/0085069 A1 | 4/2006 | Kim |
| 2006/0085070 A1 | 4/2006 | Kim |
| 2006/0085075 A1 | 4/2006 | McLeer |
| 2006/0089646 A1 | 4/2006 | Bonutti |
| 2006/0089654 A1 | 4/2006 | Lins et al. |
| 2006/0089718 A1 | 4/2006 | Zucherman et al. |
| 2006/0095134 A1 | 5/2006 | Trieu et al. |
| 2006/0106381 A1 | 5/2006 | Ferree et al. |
| 2006/0106397 A1 | 5/2006 | Lins |
| 2006/0122620 A1 | 6/2006 | Kim |
| 2006/0136060 A1 | 6/2006 | Taylor |
| 2006/0142762 A1 | 6/2006 | Michelson |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0161154 A1 | 7/2006 | McAfee |
| 2006/0264939 A1 * | 11/2006 | Zucherman et al. ............ 606/61 |
| 2007/0162000 A1 | 7/2007 | Perkins |
| 2007/0233098 A1 | 10/2007 | Mastrorio et al. |
| 2007/0270827 A1 * | 11/2007 | Lim et al. ........................ 606/61 |
| 2008/0161818 A1 * | 7/2008 | Kloss et al. .................... 606/90 |

FOREIGN PATENT DOCUMENTS

| | | |
|---|---|---|
| FR | 2 707 864 A1 | 1/1995 |
| FR | 2 717 675 A1 | 9/1995 |
| FR | 2 722 980 A1 | 2/1996 |
| FR | 2 780 269 A1 | 12/1999 |
| FR | 2 782 911 A1 | 3/2000 |
| FR | 2 806 614 A1 | 9/2001 |
| FR | 2 806 616 A1 | 9/2001 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 | 4/2001 |
| WO | WO 2006/084444 | 8/2006 |
| WO | WO 2006084444 A2 * | 8/2006 ............. A61B 17/02 |

* cited by examiner

INTERSPINOUS IMPLANT, TOOLS AND METHODS OF IMPLANTING

BACKGROUND OF THE INVENTION

With the aging of the population there has occurred an increase in the incidences of degenerative diseases of the spine and this trend is expected to continue with the continuing increase in the percentage of elderly people in the population. Spinal stenosis is one of the most frequent forms of spinal degenerative disease observed. One conventional treatment of spinal stenosis has been laminectomy and decompression of compressed vertebrae and additionally fusing the treated vertebrae if instability exists. Many potentially negative side effects are inherent in this form of treatment, including profuse bleeding, substantial risk of infection, potential nerve damage sometimes leading to paralysis and/or bladder/bowel dysfunction, dural tears, persistent fluid leakage, arachnoiditis, continuing chronic pain, non-union (if fusion is performed), fusion hardware failure, donor site pain, adjacent segment disease, long operation times, and substantial operation costs.

Additionally, there are the inherent general risks of the surgical procedure and the medical risks including, but not limited to: bleeding, infection, nerve or vessel damage, risks of anesthesia, death, need for further surgery, iatrogenic instability, epidural hematoma, failure of implants and/or associated hardware, misplacement of implants and hardware, migration of implants and hardware, heart attack, stroke, deep venous thrombosis, pulmonary embolism, spinal cord and nerve damage, reflex sympathetic dystrophy, sexual dysfunction, positioning problems, brachial plexus injuries, traction injuries, swallowing difficulties, problems with vocal cords, airway obstruction, postoperative swelling, need for prolonged intubation, persistent dural fistula, paralysis, blindness, no relief of current symptoms, possible development of new symptoms, possible worsening of current symptoms, possible need for intraoperative change of procedure, possible need for fusion of the spine as determined intraoperatively, and other rare risks not named above.

Other types of implants have been developed to distract the spinous processes without the performance of laminectomy or fusion to increase the space for existing nerves to thereby relieve pain. Implantation of these implants typically require a large incision and dissection on both sides of the spinous processes. Multiple steps of dilation and distraction are performed prior to implantation of the implant in order to finally provide a sufficient interspinous space to wedge the implant between the spinous processes. Examples of implants of these types are described in U.S. Pat. Nos. 5,496,318; 5,645,599; 5,928,232; 6,149,652; 6,514,256; 6,695,842; and 6,761,720. Further, many of these devices are rigid, inflexible and/or non-adjustable wedge-like implants that require dissection of muscle tissue and/or ligaments such as the supraspinous ligament and interspinous ligament.

In view of these and other drawbacks with using currently existing spine treatments and inter-spinous implants, there is a continuing need for improved procedures and implants to treat disorders of the spine and pain associated therewith, and particularly for treatment of degenerative spine disorders, in the elderly as well as in any other vertebrate patients. It would be further advantageous to provide implants that are implantable via minimally invasive procedures, to reduce trauma, risks of infection and costs relative to those associated with currently available procedures. Still further, it would be desirable to provide such implants to be removable (i.e., explanted), if desired, by minimally invasive procedures. The ability to adjust the amount of distraction between the spinous processes, both during initial implantation and at a later time after completion of the implantation procedure, would also be desirable. It would be further desirable to provide devices that can optionally be used in a fusion procedure.

SUMMARY OF THE INVENTION

The present invention provides devices, tools and methods for minimally invasive implantation and distraction between spinous processes for treatment of spinous disorders, and minimally invasive devices, tools, kits, systems and methods for performing fusion procedures.

An interspinous implant system for distracting and fusing at least one pair of adjacent spinous processes is provided that includes a device having: a main body including a shaft having a longitudinal axis; first and second parallel arms extending transversely from the main body, wherein at least one of the first and second parallel arms is slidably mounted with respect to the shaft; the parallel arms being configured and dimensioned to extend laterally from both sides of the spinous processes when implanted therebetween and to be inserted between the spinous processes laterally from a single side thereof; the parallel arms being variably positionable between a closed configuration, in which the parallel arms are positioned close to or in contact with one another, to facilitate insertion of the parallel arms between the adjacent spinous processes, and an open configuration, in which the parallel arms are separated from one another; and a bone ingrowth enhancing agent.

In at least one embodiment, the bone ingrowth enhancing agent comprises a particulate.

In at least one embodiment, the bone ingrowth enhancing agent comprises a plate.

In at least one embodiment, the bone ingrowth enhancing agent comprises a bone graft.

A kit for treatment of spinal disorders is provided, including: a device including: a main body including a shaft having a longitudinal axis; first and second parallel arms extending transversely from the main body, wherein at least one of the first and second parallel arms is slidably mounted with respect to the shaft; the parallel arms being configured and dimensioned to extend laterally from both sides of spinous processes of adjacent vertebrae when implanted therebetween and to be inserted between the spinous processes laterally from a single side thereof; the parallel arms being variably positionable between a closed configuration, in which the parallel arms are positioned close to or in contact with one another, to facilitate insertion of the parallel arms between the adjacent spinous processes, and an open configuration, in which the parallel arms are separated from one another; and a component for facilitating fusion of the adjacent vertebrae while the device is implanted between the spinous processes.

In at least one embodiment, the kit includes a tool for implanting the device.

In at least one embodiment, the tool for implanting the device includes: a pair of distraction arms at a distal end portion of the tool pivotally mounted for movement towards and away from one another; distal end portions of the distraction arms configured to slide over portions of the interspinous implant device to be implanted; lock arms operable to lock the distal end portions to the interspinous implant device; and a pair of drive arms at a proximal end portion of the tool connected via the pivotal mount to the distraction arms and operable to drive the distraction arms toward each other and away from one another.

In at least one embodiment, the kit includes a tool for delivering the component for facilitating fusion to a location of the adjacent spinous processes and the implant.

In at least one embodiment, the tool for delivering the component includes an elongated tube and a plunger received therein.

In at least one embodiment, the component for facilitating fusion comprises at least one of bone morphogenetic protein, bone ingrowth enhancing protein, or bone graft.

A device for distracting at least one pair of adjacent spinous processes is provided, including: a main body including a shaft having a longitudinal axis; first and second hooks extending transversely from the main body, wherein at least one of the first and second hooks is slidably mounted with respect to the shaft; the hooks being configured and dimensioned to extend laterally from both sides of the spinous processes when implanted therebetween and to be inserted between the spinous processes laterally from a single side thereof; and the hooks being variably positionable between a closed configuration, in which the parallel arms are positioned close to or in contact with one another, to facilitate insertion of the hooks between the adjacent spinous processes, and an open configuration, in which the hooks are separated from one another.

In at least one embodiment, beveled tips extend distally from the hooks.

In at least one embodiment, each of the beveled tips extends distally in a direction away from a curvature of one of the first and second hooks from which it extends, and toward the other of the first and second hooks.

In at least one embodiment, the hooks slide past one another so as to be positioned at least partially side-by side when in the closed configuration.

An interspinous implant system for distracting and fusing at least one pair of adjacent spinous processes is provided, comprising: a device including: a main body including a shaft having a longitudinal axis; first and second hooks extending transversely from the main body, wherein at least one of the first and second hooks is slidably mounted with respect to the shaft; the hooks being configured and dimensioned to extend laterally from both sides of the spinous processes when implanted therebetween and to be inserted between the spinous processes laterally from a single side thereof; the hooks being variably positionable between a closed configuration, in which the parallel arms are positioned close to or in contact with one another, to facilitate insertion of the hooks between the adjacent spinous processes, and an open configuration, in which the hooks are separated from one another; and the system including a bone ingrowth enhancing agent.

In at least one embodiment, the device includes beveled tips extending distally from the hooks.

In at least one embodiment, each of the beveled tips extends distally in a direction away from a curvature of one of the first and second hooks from which it extends, and toward the other of the first and second hooks.

In at least one embodiment, the hooks slide past one another so as to be positioned at least partially side-by side when in the closed configuration.

A kit for treatment of spinal disorders is provided, comprising: a device including: a main body including a shaft having a longitudinal axis; first and second hooked arms extending transversely from the main body, wherein at least one of the first and second hooked arms is slidably mounted with respect to the shaft; the hooked arms being configured and dimensioned to extend laterally from both sides of spinous processes of adjacent vertebrae when implanted therebetween and to be inserted between the spinous processes laterally from a single side thereof, the hooked arms being variably positionable between a closed configuration, to facilitate insertion of the parallel arms between the adjacent spinous processes, and an open configuration, in which the hooked arms are separated from one another; and the kit including a component for facilitating fusion of the adjacent vertebrae while the device is implanted between the spinous processes.

In at least one embodiment, the kit includes a tool for implanting the device.

In at least one embodiment, the tool for implanting includes: a pair of distraction arms at a distal end portion of the tool pivotally mounted for movement towards and away from one another; distal end portions of the distraction arms configured to slide over portions of the interspinous implant device to be implanted; lock arms operable to lock the distal end portions to the interspinous implant device; and a pair of drive arms at a proximal end portion of the tool connected via the pivotal mount to the distraction arms and operable to drive the distraction arms toward each other and away from one another.

In at least one embodiment, the kit includes a tool for delivering the component for facilitating fusion to a location of the adjacent spinous processes and the implant.

A method of treating spinal disorders and associated discomfort therefrom is provided, including the steps of: inserting a pair of adjacent arms between adjacent spinous processes of adjacent vertebrae of the spinal column wherein the pair of arms are inserted laterally, from a single side of the spinous processes; separating the arms in opposite directions transverse to a direction in which the arms extend; fixing the arms in a separated, configuration resulting from the separating, the arms remaining in the separated configuration as an implant; and placing a bone ingrowth enhancement agent in contact with at least a portion of both of the adjacent vertebrae and a least a portion of a device that includes the arms.

In at least one embodiment, the placing step includes delivering the agent on one lateral side of the adjacent vertebrae and device.

In at least one embodiment, the placing step includes delivering the agent on both lateral sides of the adjacent vertebrae and device.

In at least one embodiment, the placing step includes delivering a slurry of bone-ingrowth enhancing material to the vertebrae and device.

In at least one embodiment, the method includes closing an incision in a patient through which the implant and agent were delivered, after performing the inserting, separating, fixing and placing steps.

In at least one embodiment, the arms are substantially parallel to one another both before and after the separating.

In at least one embodiment, the arms comprise hooks.

In at least one embodiment, the spinous processes are not altered.

In at least one embodiment, the supraspinous ligament is maintained intact between the spinous processes.

These and other features of the invention will become apparent to those persons skilled in the art upon reading the details of the devices, tools and methods as more fully described below.

DETAILED DESCRIPTION OF THE INVENTION

Before the present devices, tools, systems and procedures are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an inter-spinous space" includes a plurality of such inter-spinous spaces and reference to the "arm" includes reference to one or more arms and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Vertebral Anatomy

Figure 1:
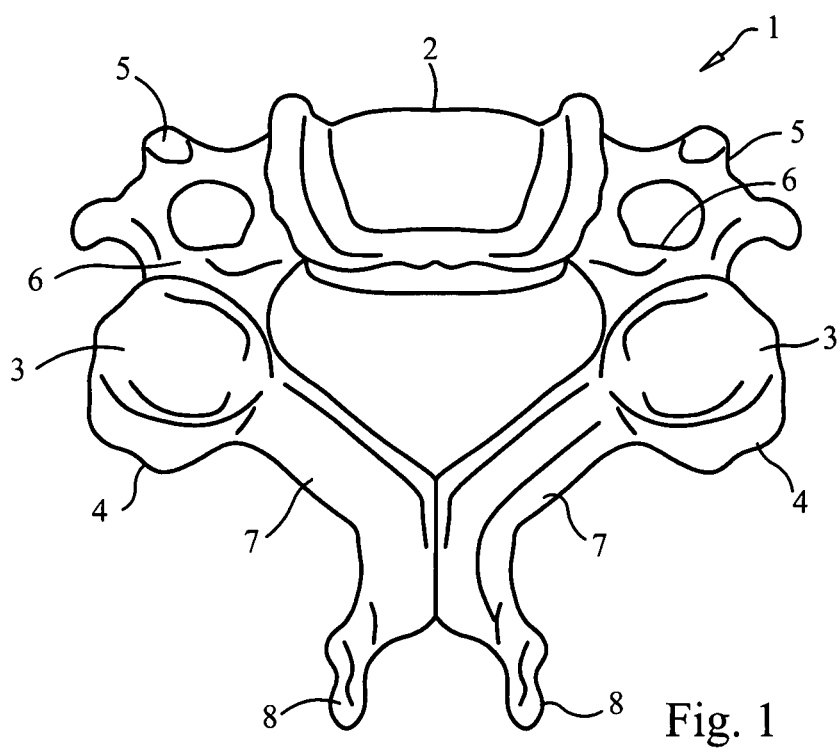
FIG. 1 is a superior view of a vertebra.

FIG. 1 is a superior view of a vertebra 1. The vertebral body 2 is an anterior portion of the vertebra and is somewhat cylindrical in shape. The intervertebral disks (not shown) are interposed between adjacent vertebral bodies in the spine. Each vertebra has two sets of facet joints 3,4, at posterior locations. One pair faces upward (superior articular facets 3) and one downward (inferior articular facets 4). There is one joint on each side (right and left). Facet joints are hinge-like and link vertebrae together. A transverse process 5 and pedicle 6 are located between the facets 3,4 and the vertebral body 2. The transverse processes 5 serve for the attachment of muscles and ligaments. The laminae 7 are plates of bone that form the posterior walls of each vertebra 2, enclosing the spinal cord. The spinous process 8 is directed backward and downward from the junction of the laminae 7, and serves for the attachment of muscles and ligaments.

Figure 2:
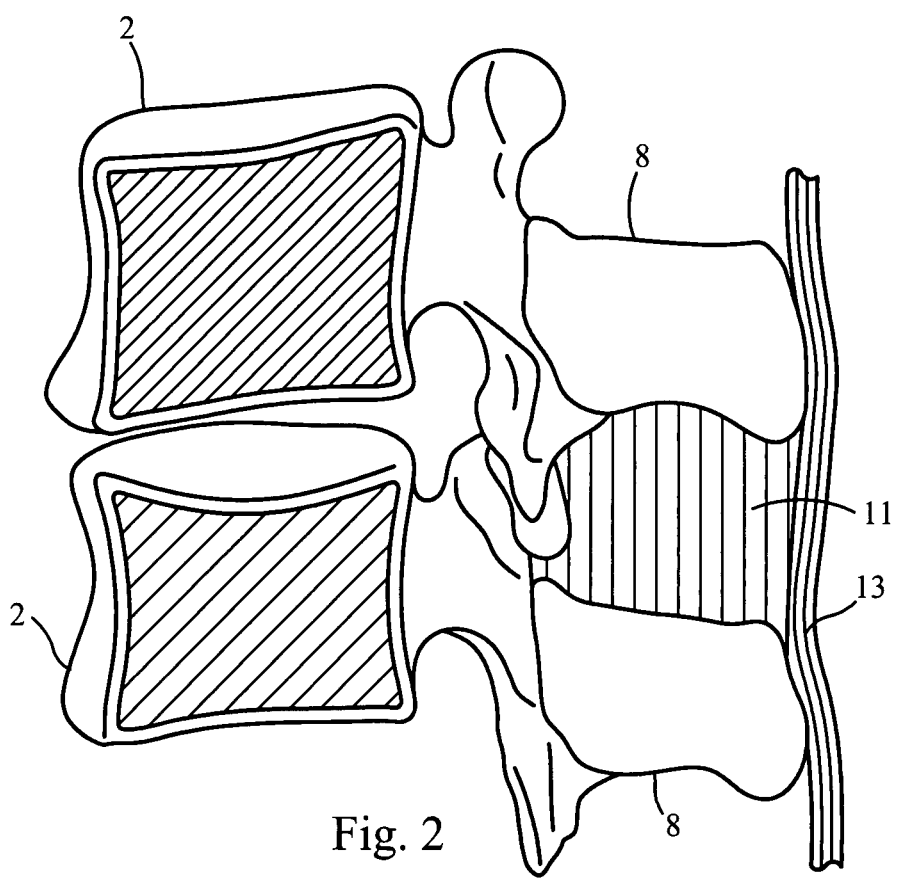
FIG. 2 is an illustration showing a lateral view of adjacent spinous processes 8,8 and a sectional view of the vertebral bodies 2 from the lumbar portion of the spine.

FIG. 2 is an illustration showing a lateral view of adjacent spinous processes 8,8 and a sectional view of the vertebral bodies 2 from the lumbar portion of the spine. FIG. 2 further illustrates interspinous ligament 11 and supraspinous ligament 13. Interspinous ligament 11 connects the adjacent spinous processes and stretches vertically from the inferior border of the upper spinous process 8 shown to the superior border of the adjacent spinous process 8 below. Interspinous ligament 11 interconnects adjacent spinous processes 8 in this manner with respect to all vertebrae, except those in the cervical spine, where it is absent. Supraspinous ligament 13 extends along the posterior tips of the spinous processes 8 and blends with the ligamentum nuchae at its superior end. In elderly individuals and in persons who engage in heavy physical activity, the ligament can become ossified, making a midline approach to the epidural space impossible.

Devices, Tools, Systems and Procedures

Figure 3A:
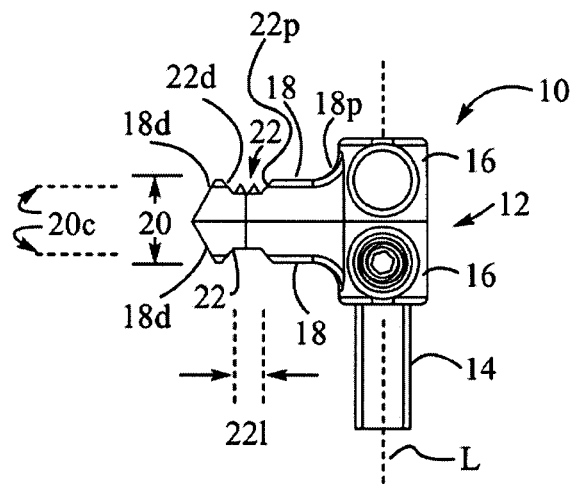
FIG. 3A shows an embodiment of an embodiment of an interspinous implant device according to the present invention.

FIG. 3A shows an embodiment of an interspinous implant device 10 according to the present invention. Device 10 includes a main body 12. Main body 12 includes a shaft 14 and bases 16 from which arms 18 extend transversely with respect to shaft 14. Arms 18 are substantially straight and typically extend perpendicularly with respect to the longitudinal axis L of shaft 14, although slight variations in this angulation can be made for variations in the embodiment shown. In any case, arms 18 extend parallel to each other. FIG. 3A shows device 10 in a closed configuration, in which the inner surfaces of arms 18 that face one another contact each other (as shown) or come into close approximation with each other, i.e., the closest configuration that arms can be positioned with respect to one another. By providing this closed configurability, arms 18 can be brought together to a smallest possible height 20 to minimize the space required between spinous processes 8,8 to allow insertion of arms 18,18 therebetween, that is, to maximize the use of device 10 for one-step insertion between spinous processes in the largest percentage of cases, down to the smallest possible distances between adjacent spinous processes.

The height of each individual arm 18 and thus the overall height 20 of the arms in the closed configuration will vary depending upon the location of the spine in which device 10 is to be inserted. However, the height 20 will be small enough to allow arms 18 to be inserted between the target spinous processes 8 where the device is desired to be implanted without the requirement for any distraction prior to this insertion. Further, height 20 in the closed configuration may be less than the distance between the two target spinous processes, or alternatively, equal or only slightly greater, such that the beveled tips of arms 18 slightly distract the spinous processes as arms 18 are inserted. Thus, device 10 can be provided in different sizes for application in different areas of the spine. For example, for insertion between spinous processes 8 in the lumbar region of the spine, device 10 will experience higher loads than a device inserted between spinous processes in the cervical region of the spine. However, the space between spinous processes is also greater in the lumbar region than in the cervical region, thereby permitting arms 18 to have greater height for devices to be implanted in the lumbar region, relative to arm heights of devices to be implanted in the cervical region. In one example, height 20 of arms 18 in the closed configuration is about 6 mm (i.e., each arm 18 having a height of about 3 mm), although this height may vary, as noted. For example, arm heights may vary from about 1.5 mm to about 6 mm, or about 2 mm to about 5 mm, depending on the intended site of implantation, typically less than or equal to about 4 mm.

On the sides of arms 18 facing away from each other (i.e., sides opposite those that abut one another or lie adjacent one another in the closed configuration, cutouts 22 may be formed and configured to receive the spinous processes 8. Thus, cutout 22 has a length 22l designed to match or slightly exceed the width of the portion of the spinous process received therein. The ends of cutout 22 may be beveled to connect with the adjacent portions of arm 18, or radiused or otherwise tapered to gradually transition to the full height of the arm. Alternatively the ends of cutout 22 can be substantially perpendicular to the lengthwise direction, wherein cutout 22 takes the form of a notch. In another embodiment, cutouts 22 are done away with altogether. However, some configuration of cutouts 22 is typically included to provide additional lateral stability. Regardless of the configuration that cutout 22 takes, the free end of arm 18 extends somewhat beyond the distal end of cutout 22 (end further from main body 12) so as to extend beyond the interspinous space when implanted, so that the protrusion extends from where the free end meets the distal end 22d of cutout against arm 18 against the lateral surface of the spinous process 8 that is opposite the lateral surface of the spinous process 8 on the side from which device 10 is inserted. Likewise, the enlarged height of arm 18 proximal of the proximal end of cutout 22 acts as a stop or anchor against the lateral surface of the spinous process 8 that is on the side from which device 10 is inserted. Thus, the spinous processes 8 are secured against lateral movements, and conversely, arms 18 are secured from sliding laterally with respect to the spinous processes 8. Bases 16 and main body 12 are positioned up against the side of spinous processes 8 to provide still further lateral stability of device 10 and the spinous processes 8 as distracted by device 10.

Figure 3B:
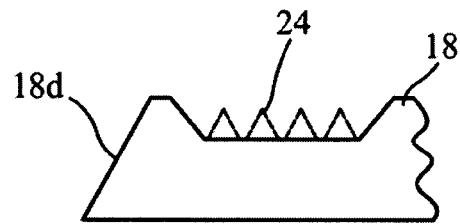
FIG. 3B is a partial view of an arm of a device according to one embodiment of the present invention.

Optionally friction-enhancing surfaces 24 may be provided on cutouts 22 to further facilitate anchoring the spinous processes. The partial view of FIG. 3B illustrates one embodiment of optional friction-enhancing surfaces 24 in the form of spikes. Alternatively, these surfaces 24 could be provided as roughened surfaces, such a knurled surfaces, threaded surfaces, diamond-cut surfaces, or the like.

The proximal end portions 18p of arms 18 can be flared, beveled or otherwise formed to have increased height, as these portions are not inserted between the spinous processes and thus do not have to be kept as thin as possible, and this provides additional support and structural rigidity where arms 18 connect to bases 16. Overall, the length of arm 18 will vary, depending upon the specific location where it is to be used (e.g., cervical spine, thoracic spine, or lumbar spine, for example), the size of the patient, as the vertebrae will vary in size based on this, and even the species of the patient, as device 10 is designed primarily for human patients, but could also be used in other vertebrates. A typical length will include a length of about four mm to about six mm, for the portion extending distally from cutout 22, plus the length of the cutout and a length of the portion of arm 18 between cutout 22 and base 16 extending about an additional ten mm to about twenty-five mm, for an overall length of about fourteen mm to about thirty-one mm, for use in the lumbar vertebrae. Of course, these lengths may be shorter for use in the cervical vertebrae as well as in the thoracic vertebrae, and may vary to be somewhat greater or lesser depending upon the anatomy of the individual patient being treated. Arms 18 are separable from each other to form a maximum open configuration height up to about eight mm to about twenty mm, typically from about twelve mm to about fourteen mm, although, again this will vary depending upon the location of the spine into which the device 10 is implanted, among other factors. Since arms 18 are continuously variably adjustable, they can be fixed at any height between the closed configuration height and the maximum open configuration height as desired. The length of cutout 22 will typically vary from about four mm to about eight mm for use in an adult male human patient, although these ranges could vary, with smaller ranges being normal for adult female human patients and even smaller ranges for pediatric patients.

The free ends (also referred to as the distal ends or leading ends) 18d of arms 18 are tapered or beveled or otherwise geometrically configured to pierce the interspinous ligament 11 during insertion and to thereby facilitate installation and placement of device 10 between the spinous processes. For example, in another geometric configuration, the distal ends of arms 18 may be tapered along more than one plane so as to resemble pencil points, or the like. Thus, arms 18, in the closed configuration are inserted through interspinous ligament 11 and positioned between spinous processes 8, preferably without distracting the spinal processes prior to inserting arms 18, although a slight amount of distraction may be performed when the closed configuration height 20 is slightly greater than the height of the space between the adjacent spinous processes 8.

In the embodiment shown in FIG. 3A, the superior base 16 is integral with shaft 14, and the inferior base 16 is slidable with respect to shaft 14 and lockable to fix it in a desired position with respect to shaft 14. The superior integral base 16 may be welded to shaft 16 or machined integrally therewith, or forged and machined as a single integral component. Shaft 14 may have a flat side 14f against which a lock can be forced to lock the position of the slidable base 16/arm 18 relative thereto. Additionally, the opening 16h that is configured to slidingly mate with shaft 14 may include a mating flat side 16f so as to key base 16 to shaft 14 to prevent rotation of base 16 and arm 18 about the longitudinal axis L of shaft 14. Further optionally, shaft 14 may include depressions 14d or through holes configured to receive a portion of a lock for enhanced prevention of sliding of the components in a vertical direction. Depressions of through holes 14d are provided on/through the flat side 14f when the flat side 14f is present.

Figure 3C:
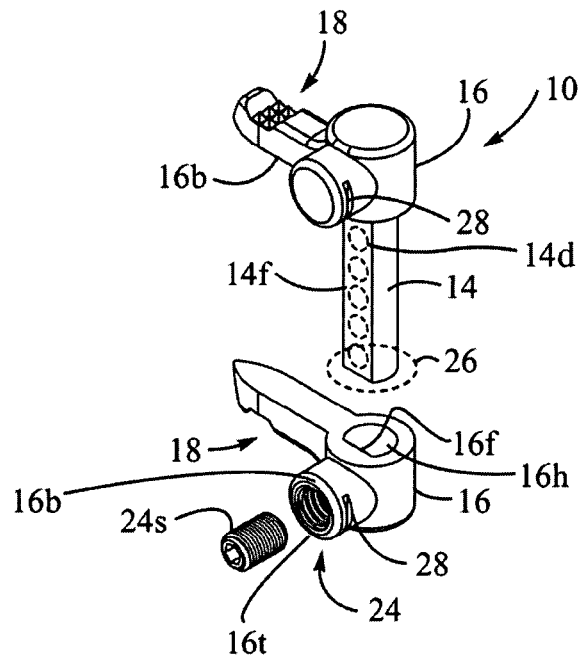
FIG. 3C is an exploded view of an embodiment of an interspinous implant device according to the present invention.
Figure 7A:
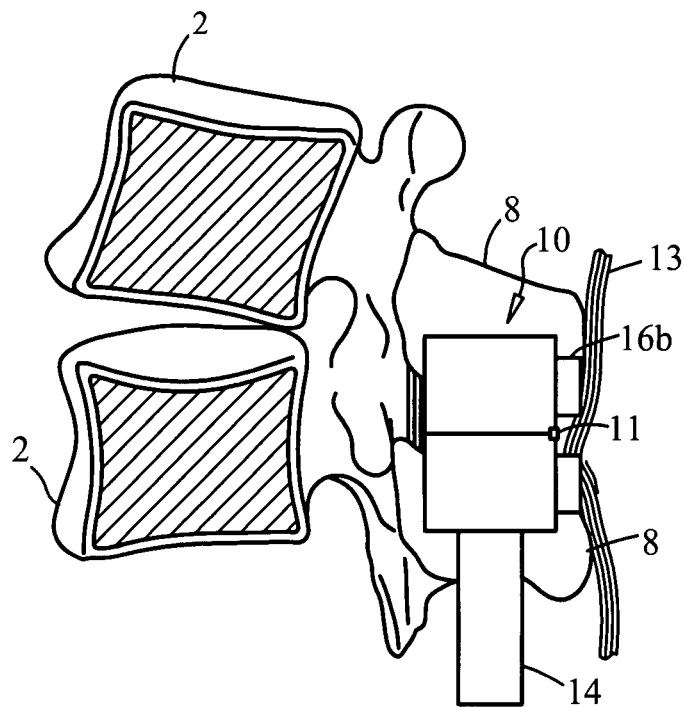
FIG. 7A illustrates a device having been inserted between the spinous processes, with the distal ends of the device arms having pierced the interspinous ligament.
Figure 7B:
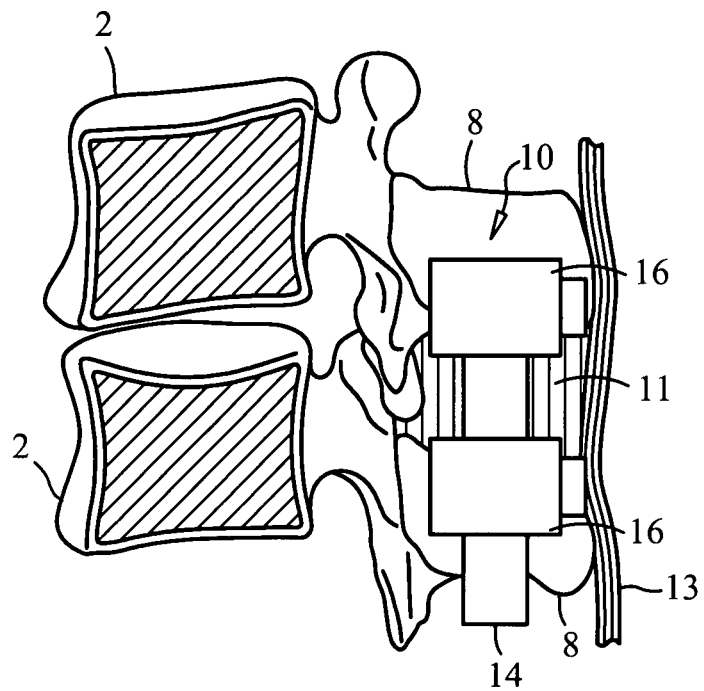
FIG. 7B illustrates a device having been successfully inserted between spinous processes, distracted to a desired height, and locked in position.

FIG. 3C is an exploded view of device 10 that illustrates the mating components for keying the inferior base 16 to shaft 14. In this embodiment lock 24 includes a set screw or locking screw 24s having external threads that mate with internal threads in a threaded opening 16t of base 16. When base 16 is assembled (slid over) on shaft 14, it is freely slidable along shaft 14 until locking screw 24s is threaded into opening 16t to an extent where the leading end of locking screw 24s extends into opening 16h and abuts against shaft 14, e.g., at flat 14f, and optionally, is received in depression or opening 14d. Thus locking screw 24s can be torqued down against shaft 14 to securely lock base 16/arm 18 in a desired location along shaft 14. As noted in FIG. 3C, device 10 can be configured so that inferior base 16/arm 18 is completely removable from shaft 14 when locking screw is in an unlocked position (i.e., not abutting against shaft 14 with sufficient force to prevent base 16 from being slid with respect to shaft 14), as base can be slid in the inferior direction until it slides off shaft 14. Alternatively, a lip or other retainer 26 may be optionally formed at the bottom end of shaft 14 to prevent base 16 from sliding off, even when in the unlocked configuration. In any of these embodiments, tool engagement structures 28 may be provided on each base for releasably locking a distraction tool thereto, as described in more detail below. In the example shown in FIG. 3C, tool engagement structures 28 are formed by slots 28. Although shown on the left sides of the bases 16 in FIG. 3C, bosses 16b may be formed on the right sides of the bases 16, such as illustrated in FIGS. 7A-7B, for example, in which case, the shaft flat 14f and openings 16f, if present, are also provided on the right side of the device 10, as well as locking and tool engagement features.

Figure 3D:
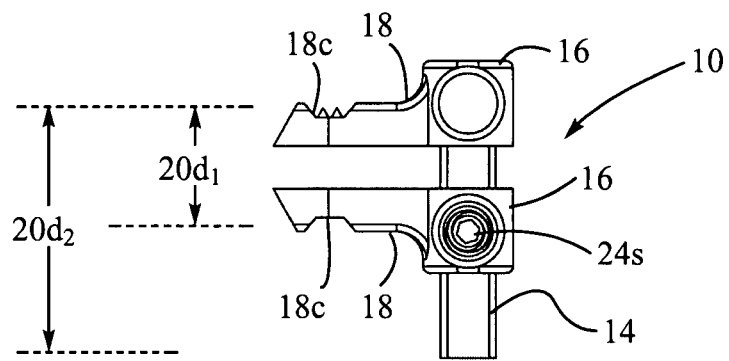
FIG. 3D shows a device in an open or distracted configuration, in which the inferior arm has been slid away from the superior arm to form a gap therebetween.

FIG. 3D shows device 10 in an open or distracted configuration, in which the inferior arm 18 has been slid away from the superior arm 18 to form a gap therebetween and so that the contact surfaces 22c of arms 18 (which, in the embodiment shown, are on cutouts 22) are separated by a distance of 20d₁. This separation distance can be locked by locking the inferior arm 16 by torquing lock screw 24s against shaft 14 in a manner as described above. Thus, inferior arm 18 is continuously positionable and lockable at any location along shaft 14 (unless depressions or holes 14d are provided, in which case a plurality of discrete, lockable positions are provided), so that the distance between contact surfaces 18c is continuously variable and lockable between and including any distance from 20c (see FIG. 3A) to 20d₂.

Alternative to the arrangements described above, device 10 may be configured so that both bases 16 are slidable and lockable with respect to shaft 14, in which case each base would include a lock 24 as described. These bases 16 may be formed to both be completely removable by sliding them off shaft 14, or one or both ends of shaft 14 may be provided with end stops, shoulders, lips or retainers 26. Any of the other variations described above may also be included in these embodiments.

Figure 4:
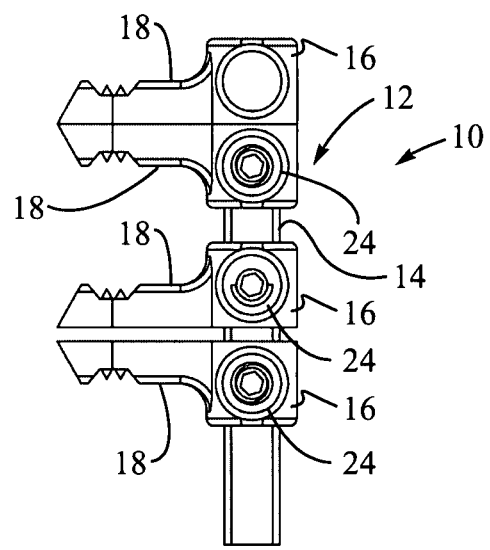
FIG. 4 shows a multi-level embodiment of an embodiment of an interspinous implant device according to the present invention.

FIG. 4 shows a multi-level embodiment of an interspinous implant device 10. In this example, main body 12 is provided with an extended shaft having sufficient length on which to mount two pairs of bases 16 having arms 18 extending therefrom. With this arrangement two levels of distraction may be implemented to the spine, a first between a first adjacent pair of spinous processes 8,8 and a second between a second pair of interspinous processes 8,8, wherein both pairs of interspinous processes may have one member that is the same. For example, the spinous process contacted on the superior surface by the inferior arm 18 of the superior pair of arms 18 may be the same spinous process that is contacted on the inferior surface by the superior arm 18 of the inferior pair of arms 18.

Like the embodiment of FIG. 3A, the superior most base 16 is integral with shaft 14 in the embodiment of FIG. 4. The other three bases 16/arms 18 are slidable with respect to shaft 14 and lockable to shaft 14 via locks 24. Alternatively, all bases 16 may be slidable with respect to shaft 14 and provided with locks 24. Further alternatively, the inferior most base 16 may be provided integrally with shaft 14, while the other three bases 6/arms 18 are slidable with respect to shaft 14 and lockable to shaft 14 via locks 24.

Figure 5A:
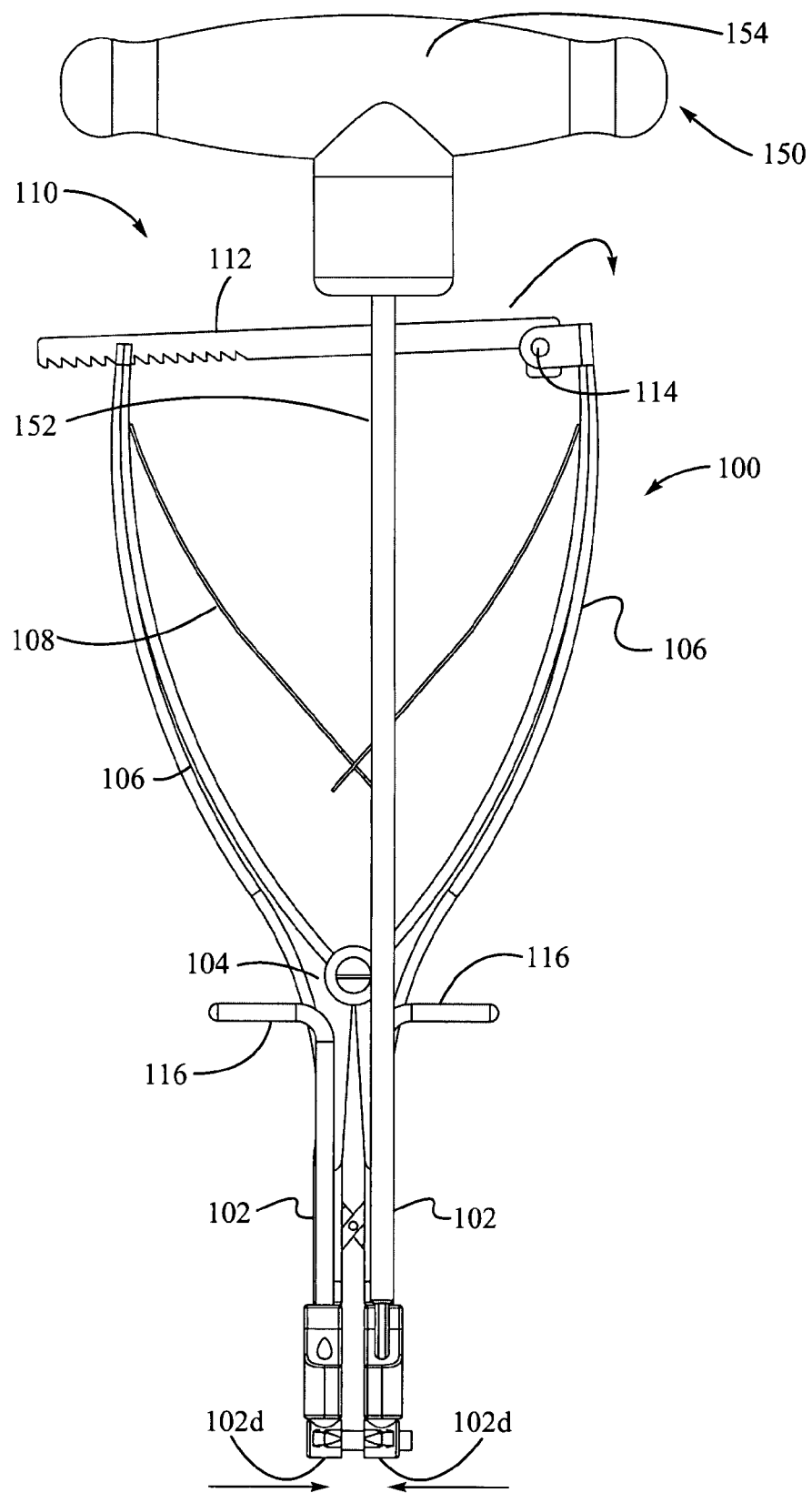
FIG. 5A is a plan view of a distraction tool and locking/unlocking tool that are useable together in the performance of an implantation of a device according to the present invention.

FIG. 5A is a plan view of a distraction tool 100 and locking/unlocking tool 150 that are useable together in the performance of an implantation of a device 10 according to the present invention. Distraction tool 100 includes first and second distraction arms 102 at a distal portion thereof, which may form a pair, and which are configured to move apart from and toward each other in the directions of the arrows shown. In this regard, distraction arms 102 are pivotally connected at a pivot joint 104 intermediate of distal and proximal ends of tool 100. Driving arms 106 extend proximally from distraction arms 102 at the location of pivot joint 104 and are movable toward one another by an operator in order to drive distraction arms 102 apart. In the example shown, driving arms 106 are integrally formed with their respective distraction arms and form the proximal portions of the integral arms, while distraction arms 102 form the distal portions of the integral arms. In the embodiment shown, the integral arms form a wishbone configuration when the distraction arms 102 are in the closed configuration, although toll 100 is not limited to this styling, as long as proximal driving arms are provided to drive distal distraction arms in a manner such as described.

Driving arms 106 may be biased apart to the closed configuration (wherein the closed configuration refers to the configuration of the distal, distraction arm members 102, which, in the closed configuration shown in FIG. 5A, drive or maintain the device arms 18 to or in the closed configuration), as illustrated in FIG. 5A, by biasing mechanism 108, which may be an arrangement of leaf springs, a single leaf spring, one or more coil springs, or other biasing arrangement, as would be apparent to those of ordinary skill in the mechanical arts. When the driving arms are pushed toward one another, as they approach one another, the pivoting action of pivot joint 104 transfers this force to the distraction arm 102 at the distal end portion of the tool 100, causing them to move apart. A distraction lock mechanism 110 may be provided to maintain the distraction arms 102 apart by the distance driven by movement together of driving arms 106. For example, in FIG. 5A, the driving arm 106 shown at the left side ratchets against a toothed rack 112 and is therefore held in position relative to the other driving arm as it is advanced toward it. This facilitates maintaining device 10 under the desired amount of distraction until the slidable arm or arms 18 can be locked in position by torquing lock screw 24 against shaft 14 as described above. After locking device 10 with the desired amount of distraction, or if the operator decides to reposition the arms and thus the amount of distraction, the operator can release the driving arms 106 to allow them to be moved apart by rotating rack arm 112 about pivot joint 114 in the direction indicated by the rotational arrow in FIG. 5A. After repositioning the driving arms as desired, rack arm 112 can be release wherein it counter-rotates to again perform the locking function described.

Figure 5B:
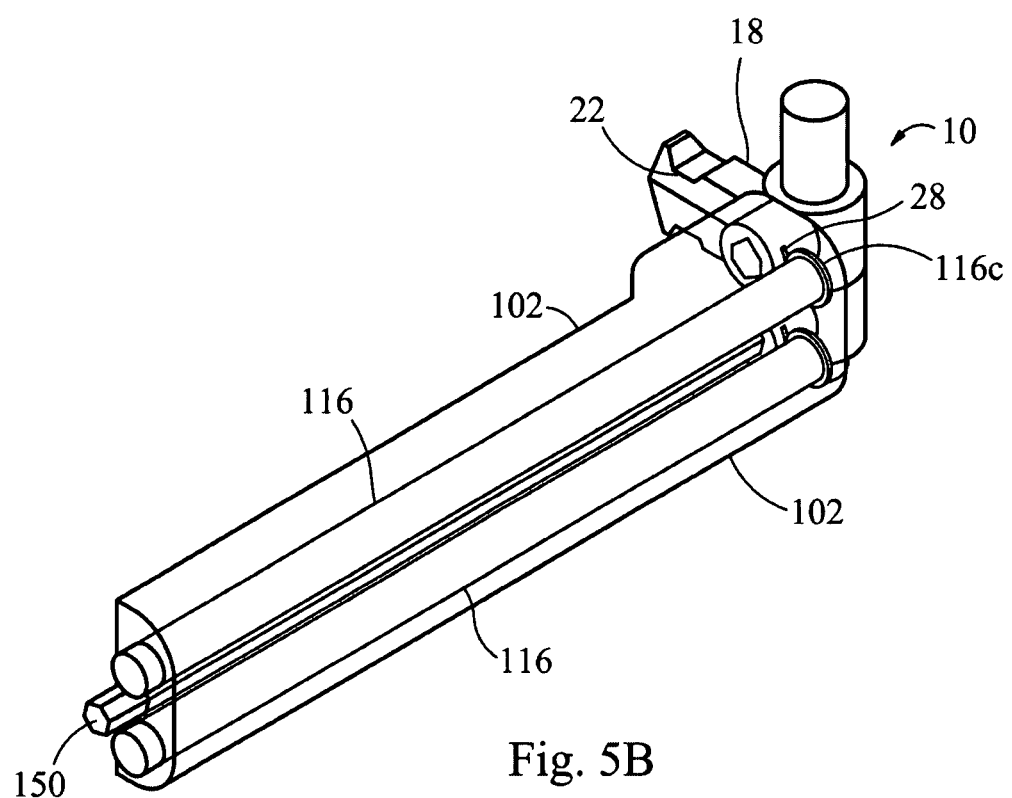
FIG. 5B is a partial, cut-away view illustrating the locking functionality of lock arms of a distraction tool.
Figure 5C:
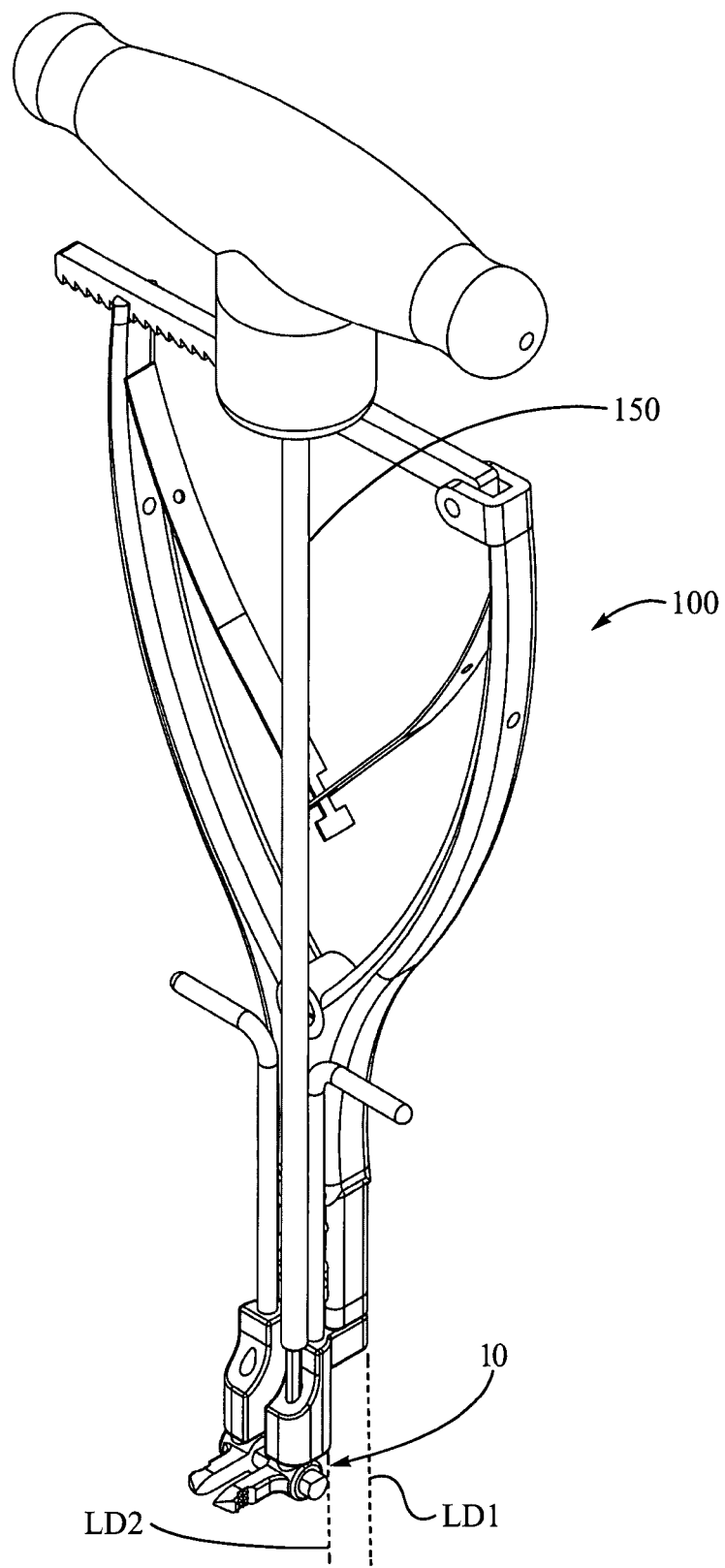
FIG. 5C is a perspective view of a device locked in a distraction tool and with a locking tool inserted.

Each distraction arm 102 has an opening in its distal end of distal end portions 102d that is configured to mate with a base 16 of device 10. As best seen in FIG. 3C, each base has a portion that extends away from the shaft to form a boss 16b. The distal end portions 102d of distraction arms 102 are tubular to slide over these bosses 16b with a close fit, but still allowing the arms 102 to slide freely over the bosses 16b. Lock arms 116 are provided with cammed or eccentric distal end pieces 116c that are configured to lock into tool engagement structures 28. FIG. 5B is a partial, cut-away view that illustrates this. Thus, after the distal ends 102d of distractor arms 102 are slid over bosses 16b of bases 16, lock arms 116 are rotated to engage cam extensions 116c into slots 28, thereby locking tool 100 against device 10, so that device 10 is captured by tool 100 for use in manipulation and implantation of device 10 as described below. FIG. 5C is a perspective view of device 10 locked in tool 100 as described. Note that although locking tool 150 is shown in both FIGS. 5A and 5C, that it is removable from distraction tool 100 and typically will not be in place when distraction tool 100 is initially mounted on device 10. Typically, locking tool 150 is inserted only after distraction tool 100 has been used to distract arms 18 apart to distract the spinous processes 8 apart to, or near to, the desired amount of distraction. This provides the surgeon with maximum visualization of the spinous processes and interspinous ligament 11, while performing piercing of the ligament, insertion/placement of device 10 and distraction of device arms 18 and spinous processes 8.

Figure 5D:
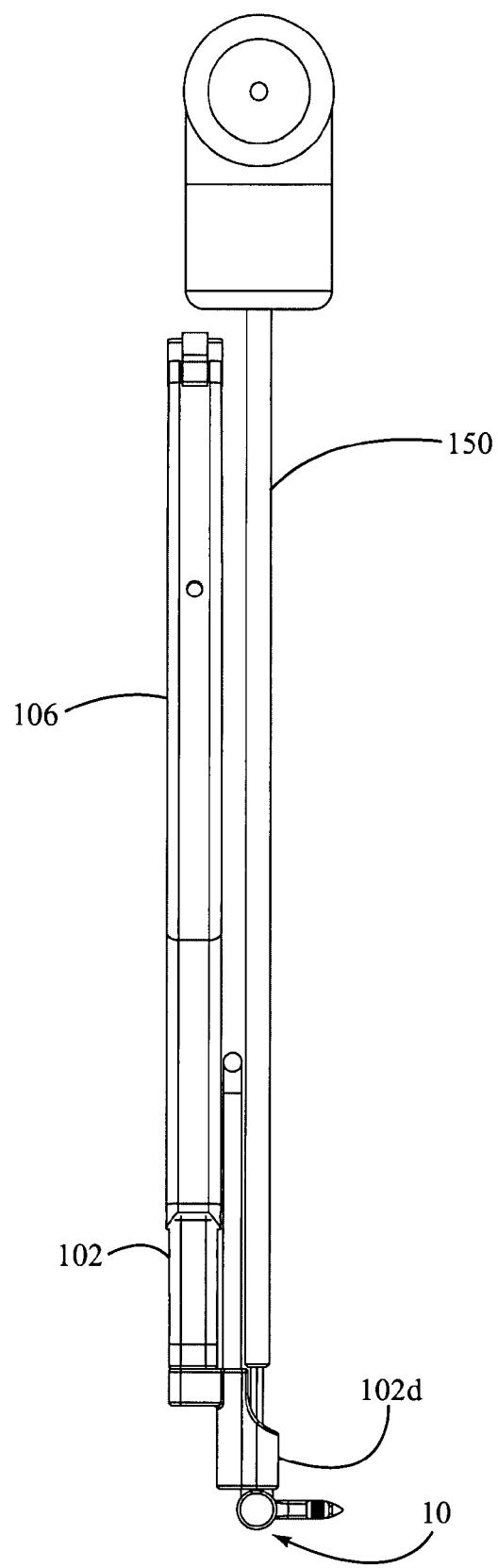
FIG. 5D is a side view of the arrangement shown in FIG. 5C.

The distal end portion 102d of each distraction arm 102 is offset from the longitudinal axis LD1 of the remainder of the distraction arm along a longitudinal axis LD2 that is parallel to LD1, as illustrated in FIGS. 5C-5D. This allows distal end portion 102d to guide the operation of locking tool 150 as it is inserted through the tubular opening at the proximal end of distal end portion 102 to engage locking screw 24 to perform a locking or unlocking operation of a base 16 to shaft 14, without being obstructed by the proximal portion of distraction arm 102 or by driving arm 106/pivot joint 104. The side view of FIG. 5D shows the clear pathway that is established for tool 150 by offsetting the distal end portions 102d, while still maintaining a low profile tool 100.

Implantation of device 10 is relatively simple compared to presently available products and can be performed as a minimally invasive procedure. It can be placed using a small unilateral incision, typically where the incision is about the same length as, or less than the height of shaft 14, and, since access to only one side of the spinal processes is required, greatly reduces the morbidity and time required to perform the implantation. Further, when a device fitted with multiple sets of arms 18 is used to treat two or three stenotic levels, for example, this results in an even greater time saving and reduction in pain, morbidity and recovery time.

For a typical procedure, during pre-operative planning, the surgeon determines the best approach (i.e., from which side of the spinous processes 8), and size of device 10 to be used, typically with the aid of radiographic imaging. The distraction tool 100 is prepared by locking closed the arms 102 relative to rack 112. The device 10 selected as the correctly sized device can be safety-checked to ensure that the slidable body 16 is freely slidable over shaft 14 when in the unlocked configuration. Device 10 is then locked to distraction tool 100 by inserting bosses 16b into the cavities in distal ends 102d and locking them therein as described herein.

Figure 6:
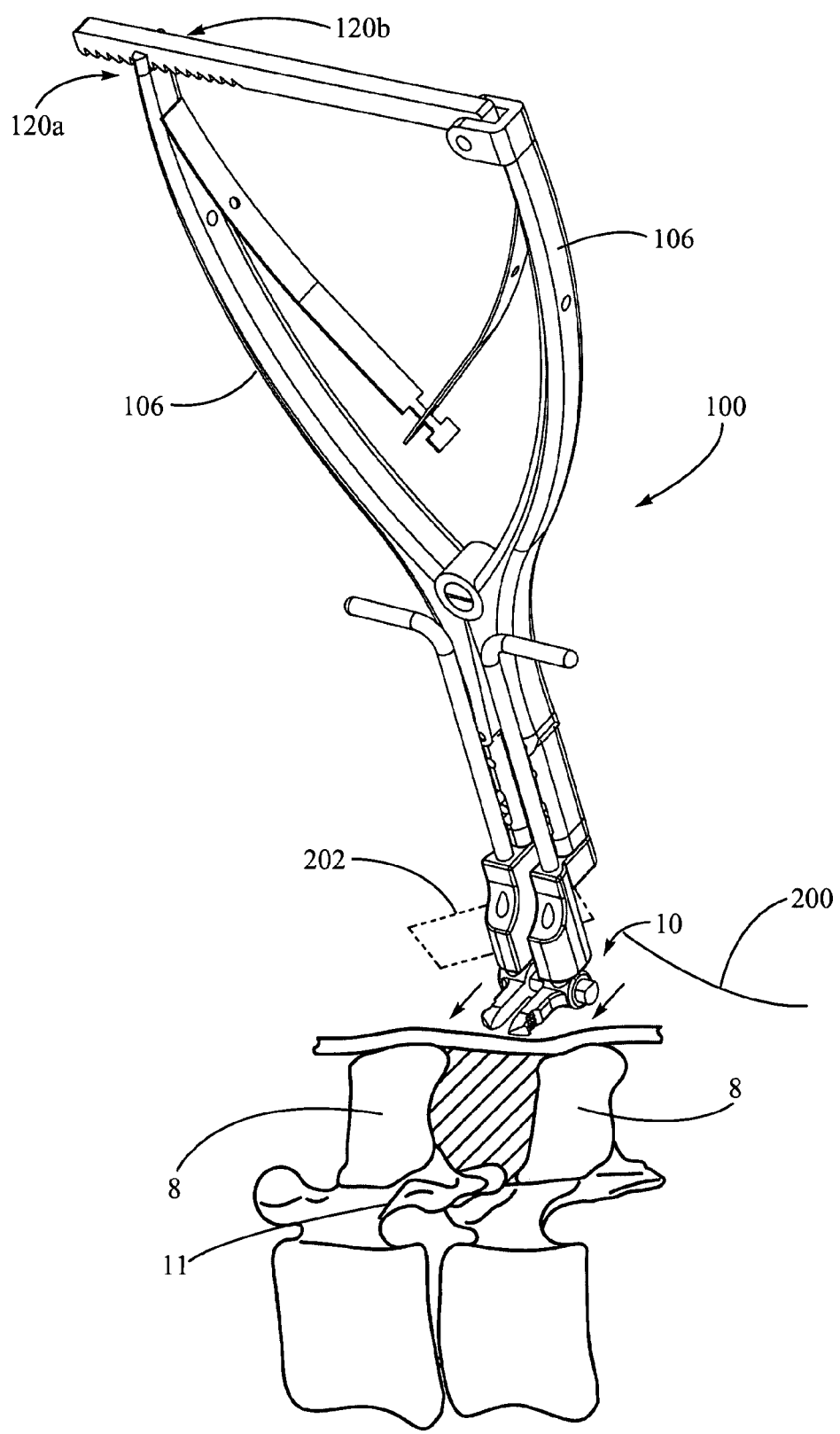
FIG. 6 illustrates use of tool 100 for insertion and initial placement of a device.

After the making the incision 202 in the patient 200 in a location to access one side of the spinal processes to be treated, dissection is performed to provide lateral access to the spinal processes 8, 8 and interspinous ligament 11 from one side only. Prior to this, device 10 will have been mounted on tool 100 and locked in place in the closed configuration as shown in FIG. 6 and in a manner as described above. Device 10 is then inserted through the incision 202, using tool 100, and the distal/free ends of arms 18 are approximated to the interspinous ligament joining the two target spinous processes, from a lateral approach, as illustrated in FIG. 6. Tool 100 is then used to drive the free ends of arms 18 through the interspinous ligament 11, thereby piercing it, but preserving the interspinous ligament intact between the processes 8. Also, the supraspinous ligament may be left intact and need not even be pierced or altered. Thus, free ends of arms 18 extend out of the opposite side of the interspinous space between spinous processes 8,8, beyond ligament 11. It is noted that device 10 is designed to be placed between the interspinous processes without the need for any preliminary distraction, prior to insertion of device 10. However, in the unlikely situation where there is not enough space to insert device 10 initially between spinous processes, one or more dilators may be used to perform preliminary dilation in one or more iterative dilation steps. FIG. 7A illustrates device 10 having been inserted between the spinous processes 8, with the distal ends of arms 18 having pierced the interspinous ligament. At this stage of the procedure, tool 100 will still be locked to device 10, but tool 100 is not shown in FIG. 7A for clarity of illustration of device 10 relative to the anatomy.

Once device 10 has been successfully inserted between the spinous processes (e.g., where cutouts 22 are aligned with the respective processes 8 to be distracted), locking tool 150 may optionally be inserted into a distal end portion 102 that is joined with a slidably adjustable base 16. Alternatively, insertion of locking tool 150 can be inserted earlier in the process. Preferably, however, distraction of the spinous processes is performed first, by distracting arms 18 apart using tool 100, and once the desired amount of distraction has been reached or approximated, locking tool 150 is then inserted. In any case, tool 100 is manipulated to squeeze drive arms 106 together so as to drive arms 18 of device apart, via distraction arms 102 in a manner described above. Note that an indicator 120 may be provided on the proximal end portion of tool 120, that can be viewed by the user to tell the user the precise amount of distraction as the distance between arms 106 is varied to vary the amount of distraction. In the example of FIG. 6, an indicator needle 120a is provided to extend from one of the drive arms 106 to indicate the amount of distraction where it aligns with graded markings 120b along rack 112.

The amount of distraction effected will depend on different variables, including the degree of deterioration or other malady causing the patient's discomfort, the location of the vertebra/spinous processes being distracted, the age, sex, and/or species of the patient, etc. Typically distraction amounts may be in the range of about three to about fifteen millimeters, or about five to about fifteen millimeters, or from the height of the arms in the closed configuration up to about twenty-two millimeters, for example, although these ranges may vary depending on, but not limited to the factors mentioned above. The distraction provided is a controlled, gradual retraction since the arms 18 of device 10 can be spread gradually, smoothly, and as slowly as desired. Optionally, it is possible to lock in a first distraction amount for a period of time, and then unlock the device 10 to increase the amount of distraction and lock in this new, greater amount of distraction. This process can be iterated as many times as desired to provide a slow and gradual widening of the space between the spinous processes, if desired.

Figure 7C:
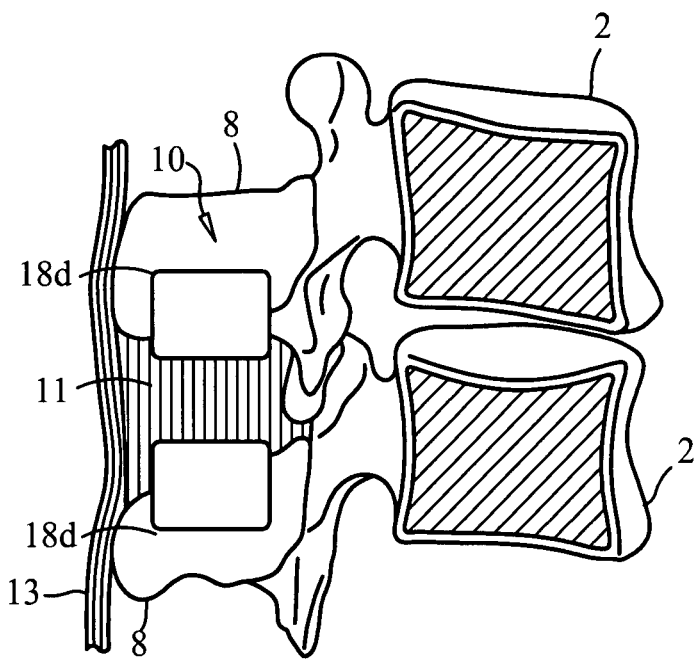
FIG. 7C illustrates an opposite side view of FIG. 7B.

In any event, once device 10 has been positioned to provide the desired amount of distraction (amount by which the spinous processes are forced apart), tool 150 is used to lock movable base 16 against shaft 14 to maintain arms 18 in their current configuration. Lock arms 116 can then be reverse rotated to unlock tool 100 from device 10 and tool 100 and tool 150 can be removed together. Alternatively, tool 150 can be removed prior to removing tool 100. Tool 150 has a shaft 152 and a handle 154 that can be torqued by the user to effect a locking or unlocking of the lock 24 on base 16. Shaft 152 preferably exceeds the length of tool 100 so that handle 154 can be torqued without interference from tool 100. The distal end of tool 150 is configured to mechanically mate with locking screw 24s to provide the torquing forces necessary to lock locking screw against shaft 14 or to release locking screw 24s from contact with shaft 14, thereby unlocking base 16 and allowing it to slide with respect to shaft 14. For example, locking screw may be provided with a female hex head and the distal end of tool 150 would then be provided with a mating hexagonal male configuration. Other screw head mating configurations may be substituted, as well as other mating mechanical configurations, as would be readily apparent to those of ordinary skill in the mechanical arts. FIG. 7B illustrates device 10 having been successfully inserted between spinous processes 8, distracted to a desired height, and locked in position, in a manner as described above. Thus, FIG. 7B shows device 10 after removal of the implantation tools, after which the surgical site can be closed to complete the procedure, leaving device 10 in position as shown in FIG. 7B. FIG. 7C illustrates an opposite side view of FIG. 7B, wherein the distal end portions 18d of arms 18 are shown protruding through the opposite side of the interspinous ligament and arms 18 are distracting the interspinous processes apart by a desired amount.

In procedures where more than one level of dysfunction is to be treated, and thus at least two pairs of adjacent spinous processes 8 are to be distracted, the procedure is similar, although a slightly longer incision 202 may need to be placed. Further, the one or more pairs of arms 18/bases 16 that are not initially locked to tool 100 must be locked against shaft 14 in the closed configuration, at a distance/distances from the pair of bases that are locked into tool 100 so as to align with the appropriate interspinous spaces into which they are to be placed. Each pair of arms 18 can then be driven sequentially into the respective target interspinous space using tool 100. Distraction may be performed at the time of placing each respective pair of arms, or the surgeon may wait until all pairs of arms have been pierced through the interspinous ligaments 11 in the respective target interspinous spaces, and then go back and perform the distraction of each pair of arms 18 sequentially. A still further alternative is to lock multiple tools to a multi level device 10, where each pair of arms 18 are locked to an individual tool 100. Further alternatively, tool 100 may have multiple sets of arms 102, each set being lockable to a respective level (i.e., pair of arms 18) of the device 10, prior to insertion of the device. The respective sets of arms are movable with respect to one another in a direction along the longitudinal axis of shaft 14. This allows alignment of the respective pairs of arms 18 with the spaces between the spinous processes to be treated. In this case piercing of the ligaments is preformed with all sets of arms during the same step, with a parallel type of movement of the sets of arms 18 through the ligaments 11,13 in the respective interspinous spaces. Subsequently, the distraction and locking of the arms can be performed sequentially.

In any of the above-described procedures, after the desired amount of distraction has been effected against each pair of adjacent target spinous processes and all bases 16 have been locked to maintain the desired distraction level(s), tools 100 and 150 are removed and the patient is closed up (including closing the incision 202) to complete the procedure. At a later time, the site can be re-entered to adjust one or more distraction levels, by locking tool 100 against the bosses 16b of the bases from which the arms 18 to be adjusted extend, and then using tool 150 to unlock a base 16 and adjust the amount of distraction as desired. The base 16 can then be relocked and the tools can be removed and the patient closed, in the same manner as described previously.

Device 10 can also be removed, if desired, by entering the patient in the same manner described above, and locking tool 100 to device 10. Tool 150 is then used to unlock base 16 and tool 100 is used to retract arms 18 back together to the closed position. Base 16 is then relocked to maintain the arms 18 in the locked configuration and tool 150 is used to pull (retract) device out from between the spinous processes 8. Tool 100 and device 10 can then together be removed from the patient and the patient can be closed to finish the procedure. Alternatively, another device 10 may be implanted to replace the device 10 that was removed.

Optionally, device 10 may be used in the performance of a fusion procedure. In this case, device 10 is implanted in any of the same manners described above. Once device 10 has been placed, distracted to the amount desired and locked to maintain the desired amount of distraction, the device implantation tools 100,150 can be removed and portion of the lamina 7 and spinous processes 8 may optionally be decorticated, using a high speed burr, for example, to encourage bone growth/regeneration/healing process, and a protein substance, such as bone morphogenetic protein (BMP), one or more bone grafts (either solid or particulate) or other bone growth enhancing material or agent 30 is implanted into the surgical site to contact at least a portion of device 10 and portions of both of the vertebrae 1 spanned by device 10 as well as lamina 7. Portions or all of device 10 may be covered/encapsulated by the bone growth enhancing material 30, with material 30 also contacting and covering at least portions of the spinous processes 8 that are contacted by device 10 and/or laminae 7 of those same vertebrae 7. Upon closing up the patient, the soft tissues surrounding the bone growth enhancing material 30 maintains the material 30 in place to allow tissue ingrowth to proceed in the desired locations.

Figure 8A:
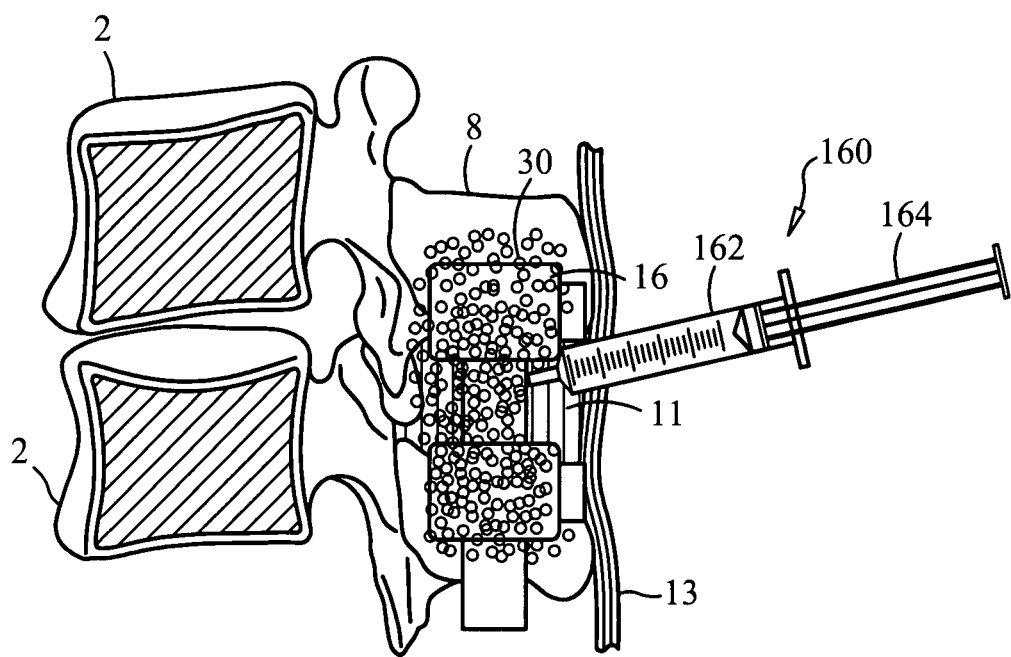
FIG. 8A illustrates implantation of a slurry of bone ingrowth material after placement of the device.

FIG. 8A illustrates implantation of a slurry of bone ingrowth material 30 after placement of device 10. In this case, the slurry is delivered via a delivery device 160 having a tube 162 that contains the slurry and a piston/plunger component 164 used to drive the material 30 out of the larger bore distal end of tube 162 when the distal end has been placed in the surgical site at a location where it is desired to deliver the bone ingrowth enhancing material 30. Tool 160 may be very similar to a standard syringe, for example, but with an open bore at the distal end, so that the distal opening has an inside diameter the same, or only slightly smaller than the inside diameter of the tube 162. Other tools may be used for delivery of the bone ingrowth enhancing material, as would be readily apparent to one of ordinary skill in the biomechanical arts. The material can be spread using a spatula or other similar tool (not shown) if desired to facilitate further placement as desired. By filling the space with the material 130, it remains packed in place once the surgical site is closed. As noted previously, solid ingrowth materials 30, such as bone grafts, plates or the like may be implanted additionally, or alternatively to the particulate material. After completion of the implantation of the ingrowth enhancing material(s) 30, the site is closed around the materials, to maintain them relatively motionless to enhance the ingrowth of bone tissue therein.

Figure 8B:
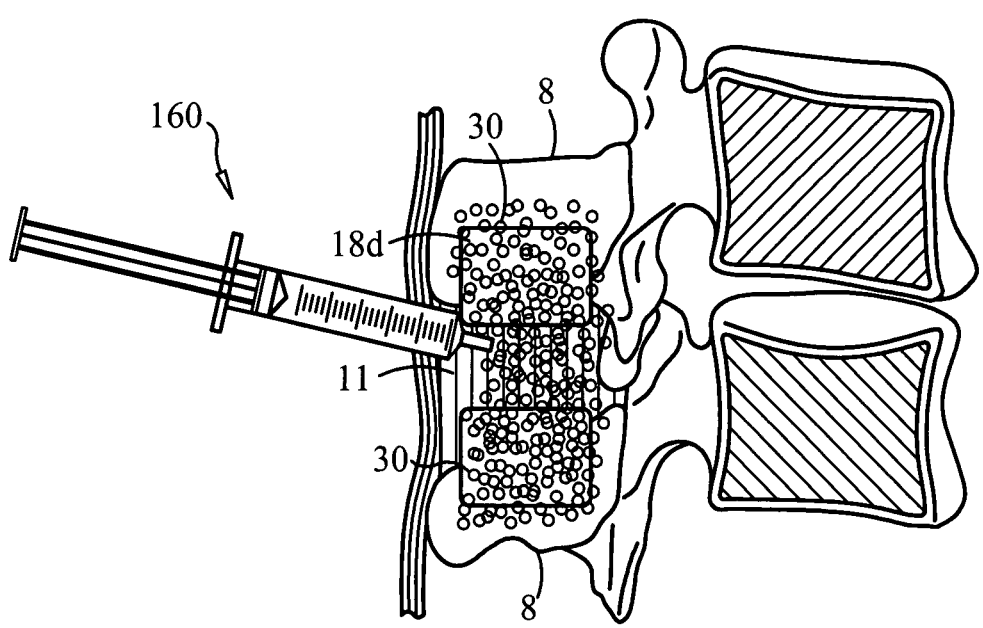
FIG. 8B illustrates an optional step of placing bone ingrowth enhancing material on the opposite lateral side of the device and vertebrae.

Optionally, bone ingrowth enhancing material 30 may also be implanted, by opposite lateral side of the device 10 and vertebrae 1, as illustrated in FIG. 8B. This placement of the material 30 on the opposite side may be performed similar to that performed on the first side, with the material contacting and at least partially covering the distal end portions 18 and the spinous processes 8 and/or laminae 7. The placement of the material may be performed using minimally invasive techniques, such as by using tool 160 for delivery of slurry or particulate material 30, with or without further spreading with a spatula or the like. Delivery of material 30 to both side of the device 10 and vertebrae 1 can be performed from the single entry incision having been established at the beginning of the implantation procedure. Of course the lamina on the opposite side would also need to be exposed and prepared to facilitate a healing response such as with a high speed burr or the like, as described above.

In any of the above examples, after closure of the surgical site, device 10 maintains the spinal processes 8 a fixed distance apart, and by immobilizing the spinal processes by providing posterior fixation, this decreases spinal segment motion and allows bone ingrowth to occur to fuse the adjacent vertebrae and device 10 together.

Figure 9:
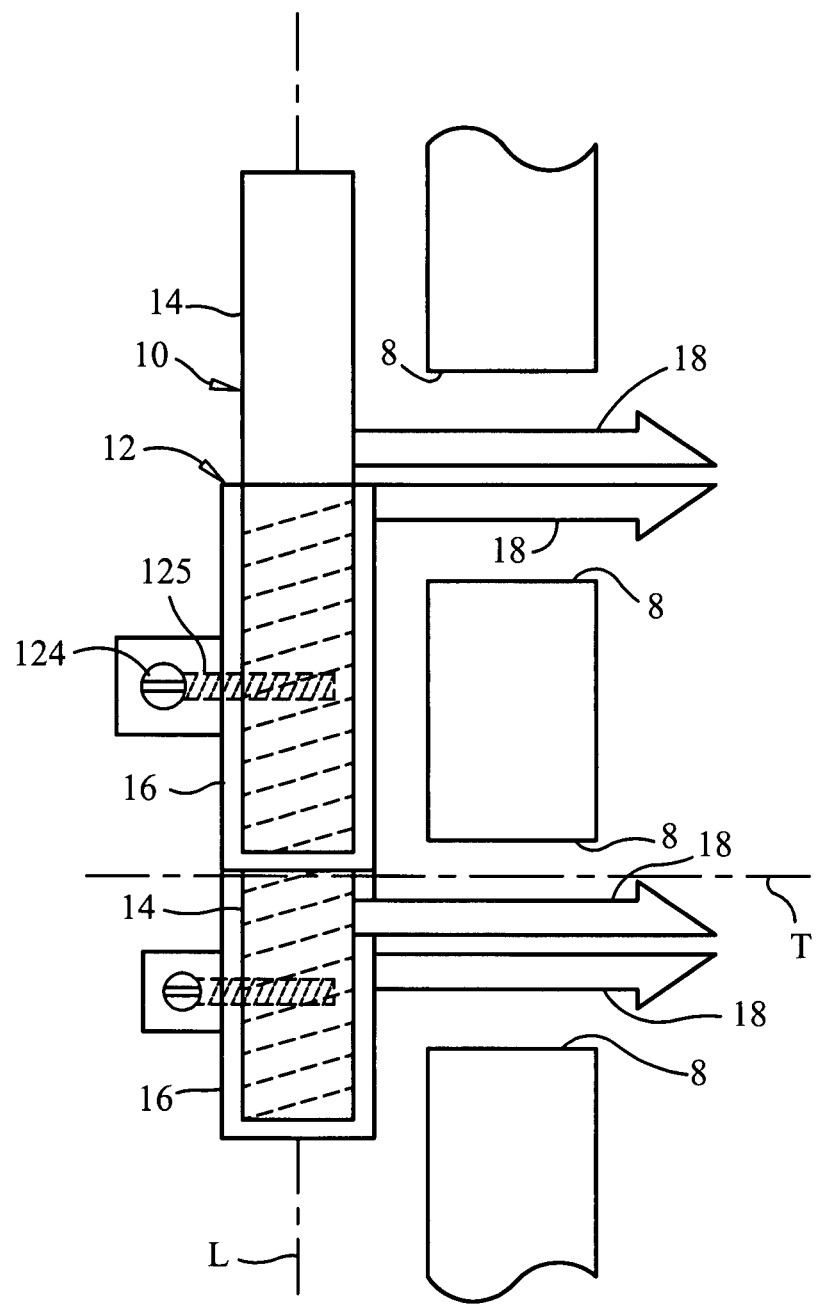
FIG. 9 schematically illustrates another embodiment of a device according to the present invention.

FIG. 9 schematically illustrates an alternative embodiment of a device 10. While the example shown is a multi-level distraction implant device for distracting adjacent pairs of adjacently opposed spinous processes 8, a single level device 10 may also be provided using similar construction, but only one pair of arms 18 for distraction a single pair of spinous processes. Also, like the embodiments described previously, device 10 may be configured to distract between two or more non-adjacent pairs of adjacently opposed spinous processes 8. Each pair of arms in this embodiment has one arm 18 that extends directly from shaft 14 of main body 12, while the other arm 18 of the pair extends from base 16. Drivers 124 are provided and configured to be torqued by a driving tool (e.g., such as tool 150, for example) to drive arms 18 toward each other or apart from each other, depending upon the direction of torquing. Each pair of arms is driven by a separate driver 124, respectively. Driver 124 may be threadably engaged with gearing 125, such as racking and pinion, a worm gear, splines or other gearing arrangement, for example. Gearing 125 engages with threading, rack, etc, on shaft 14 so that as driver 124 is torqued, gearing 125 translates this torque to shaft 14 to move it either up or down with respect to the base 16 into which it is inserted, and consequently either driving arms 18 apart or towards one another. Device 10 is inserted laterally so that each pair of arms 18 pierces through the interspinous ligament 11 in the interspinous space between the spinous processes to be distracted.

Also like the previously described devices, these alternative devices can be used in the performance of a fusion, using bone ingrowth enhancing material 30 in any of the manners described above.

Figure 10:
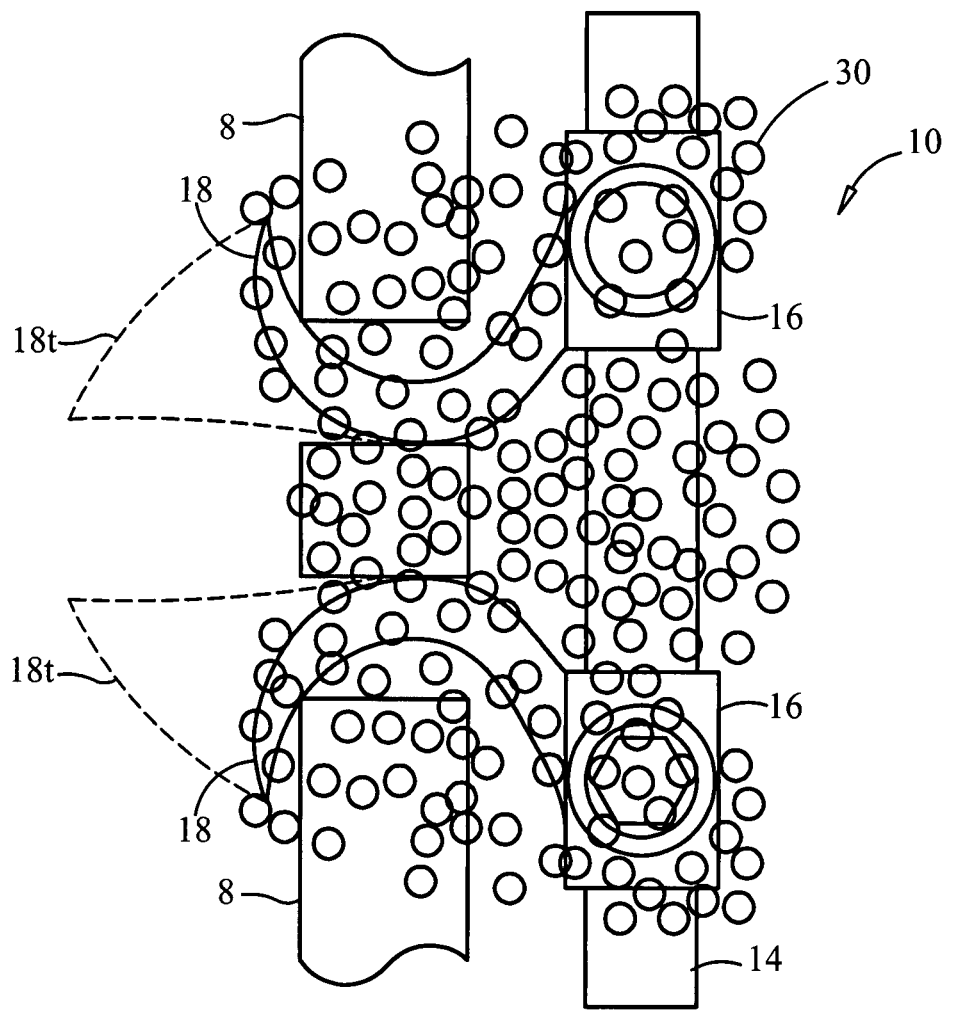
FIG. 10 illustrates an alternative embodiment of a device according to the present invention.

FIG. 10 illustrates an alternative embodiment of device 10, in which device 10 includes bases 16 that slide on shaft 14 in the same manner and using the same mechanisms as those described above with regard to the embodiments described in FIGS. 3A-8B. In FIG. 10 however, arms 18 are hooks that are substantially curved or "hook-shaped". FIG. 10 illustrates hooks 18 having been inserted through the interspinous ligaments 11 at adjacent levels of the vertebrae, between spinous processes 8. Thus, a multi-level distraction is illustrated in FIG. 10, with a spinous process 8 being positioned between the hooks 18. Due to the curvature of the hooks 18, one or more dilators may be used to perform preliminary dilation/distraction in one or more iterative dilation steps, prior to insertion of the hooks 18 between spinous processes 8. Optionally, beveled tip portions 18t may be provided at the distal ends of hooks 18 in order to better align the distal tips of hooks 18 with the spaces between the spinous processes, and to provide a small-cross sectional area tip on each hook to perform the initial piercing through the interspinous ligament. Each beveled tip 18t extends in a direction away from the curvature of the hook 18 that it extends from and toward the opposite hook 18, so that the distal end of tips 18t are much closer to one another than the ends of the hooks from which they extend. The beveled portions of tips 18t then act to perform some distraction as tips 18t are passed between the spinous processes, thereby guiding hooks 18 into positions between the spinous processes 8. Device 10 may then be adjusted to perform the desired amount of multi-level distraction using the same techniques and tools described above. The procedure can then be completed at this stage, once arms 18 have been locked at the desired relative positions. Alternative, device 10 can be used in the performance of a fusion, using bone ingrowth enhancing material 30 in any of the manners described above, as illustrated in FIG. 10.

Figure 11:
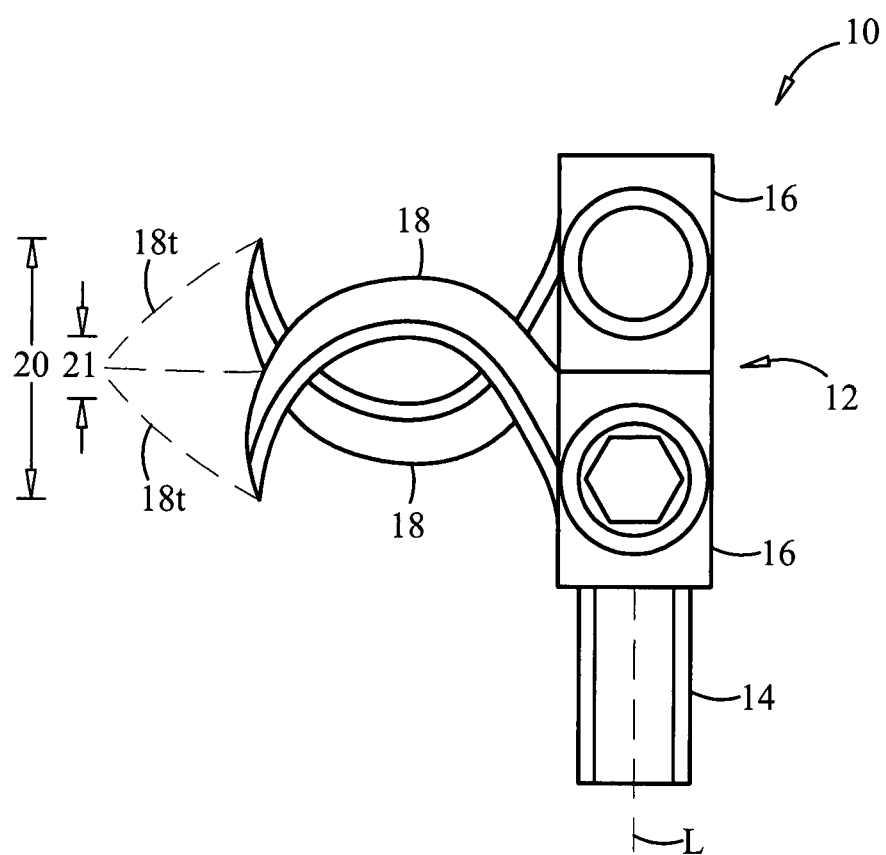
FIG. 11 illustrates an alternative embodiment of a device according to the present invention.

FIG. 11 illustrates an alternative embodiment of device 10, in which device 10 includes bases 16 that slide on shaft 14 in the same manner and using the same mechanisms as those described above with regard to the embodiments described in FIGS. 3A-8B. In FIG. 11 arms 18 are hooks that are substantially curved or "hook-shaped", and rather than being aligned so that that abut one another in the closed configuration like arms 18 of FIG. 3A, hooks 18 are slightly offset to allow hooks 18 to slide past one another in the closed configuration shown in FIG. 11. This greatly reduces the height 20 in the closed configuration, relative to what it would be if hooks 18 were aligned to abut one another in the closed configuration. The configuration in FIG. 11 makes it possible to use device 10 at a single level, i.e., where no spinous processes 8 are positioned between the adjacent hooks. Thus device 10 of FIG. 11 can be inserted and used in any of the same manners described above with regard to FIGS. 3A-8B. Due to the curvature of the hooks 18, one or more dilators may be used to perform preliminary dilation/distraction in one or more iterative dilation steps, prior to insertion of the hooks 18 between spinous processes 8. Optionally, beveled tip portions 18t may be provided at the distal ends of hooks 18 in order to better align the distal tips of hooks 18 with the space between the spinous processes, and to provide a small-cross sectional area tip on each hook to perform the initial piercing through the interspinous ligament. Each beveled tip 18t extends distally in a direction away from the curvature of the hook 18 that it extends from and toward the opposite hook 18, so that the distal ends of tips 18t are much closer to one another than the ends of the hooks from which they extend and are very close together when hooks 18 are in the closed configuration shown in FIG. 11, such that height 21 is much less than a distance of a space between adjacent spinous processes, for example, less than about 3 mm, or less than about 2 mm or less than about 1 mm. The beveled portions of tips 18t then act to perform some distraction as tips 18t are passed between the spinous processes 8, thereby guiding hooks 18 into positions between the spinous processes 8 at the same level, so that hooks 18 engage adjacent spinous processes. Device 10 may then be adjusted to perform the desired amount of distraction using the same techniques and tools described above. The procedure can then be completed at this stage, once arms 18 have been locked at the desired relative positions. Alternatively, device 10 can be used in the performance of a fusion, using bone ingrowth enhancing material 30 in any of the manners described above.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An interspinous implant system for distracting and fusing at least one pair of adjacent spinous processes, said system comprising:
    a device including:
    a main body including a shaft having a longitudinal axis;
    first and second bases connected to said main body;
    first and second arms rigidly and fixedly connected to said first and second bases, respectively and extending from said bases, transverse to said longitudinal axis, wherein at least one of said first and second bases is slidably mounted on said shaft;
    said arms being integrally formed and rigid, with no moving parts, and configured and dimensioned to extend laterally from both lateral sides of the spinous processes when implanted therebetween and to be inserted between the spinous processes laterally from a single side thereof;
    said first arm having a first curvature along a top side of said first arm, said first curvature facing in a first direction parallel to said longitudinal axis of said main body, and a bottom side of said first arm opposite said first side extending straight and substantially perpendicular to said longitudinal axis;
    said second arm having a second curvature along a bottom side of said second arm, said second curvature facing in a second direction opposite to said first direction and parallel to said longitudinal axis of said main body, and a top side of said second arm opposite said bottom side extending straight and substantially perpendicular to said longitudinal axis;
    said arms being variably positionable between a closed configuration, in which said arms are positioned so that said bottom side of said first arm contacts and closes against said top side of said second arm, to facilitate insertion of said arms between the adjacent spinous processes from one side of the spinous processes, and an open configuration, in which said arms are separated from one another.

2. The system of claim 1, further comprising a bone ingrowth enhancing agent, wherein said bone ingrowth enhancing agent comprises a particulate.

3. The system of claim 1, further comprising a bone ingrowth enhancing agent, wherein said bone ingrowth enhancing agent comprises a plate.

4. The system of claim 1, further comprising a bone ingrowth enhancing agent, wherein said bone ingrowth enhancing agent comprises a bone graft.

5. A kit for treatment of spinal disorders, said kit comprising:
    a device including:
    a main body including a shaft having a longitudinal axis;
    first and second bases connected to said main body; and
    first and second parallel arms each having a distal end and a proximal end, respectively, said first and second parallel arms being rigidly and fixedly connected to said first and second bases via said proximal ends, respectively, and wherein said distal ends are free ends, respectively, said parallel arms extending transversely from said main body, relative to said longitudinal axis, each of said parallel arms being rigid with no moving parts relative to said base that each said parallel arm is connected to, respectively, wherein at least one of said first and second bases is slidably mounted on said shaft;
    said parallel arms being configured and dimensioned to extend laterally from both sides of spinous processes of adjacent vertebrae when implanted therebetween and to be inserted between the spinous processes laterally from a single side thereof;
    said parallel arms being variably positionable between a closed configuration, in which said parallel arms are positioned in contact with one another, to facilitate insertion of said parallel arms between the adjacent spinous processes, and an open configuration, in which said parallel arms are separated from one another; and
    a component for facilitating fusion of the adjacent vertebrae while said device is implanted between the spinous processes.

6. The kit of claim 5, further comprising:
    a tool for implanting said device.

7. The kit of claim 6, wherein said tool comprises:
    a pair of distraction arms at a distal end portion of said tool pivotally mounted for movement towards and away from one another;
    distal end portions of said distraction arms configured to slide over portions of the interspinous implant device to be implanted;
    lock arms operable to lock said distal end portions to the interspinous implant device; and
    a pair of drive arms at a proximal end portion of said tool connected via the pivotal mount to said distraction arms and operable to drive said distraction arms toward each other and away from one another.

8. The kit of claim 5, further comprising a tool for delivering said component for facilitating fusion to a location of the adjacent spinous processes and said implant.

9. The kit of claim 8, wherein said tool comprises an elongated tube and a plunger received therein.

10. The kit of claim 5, wherein said component for facilitating fusion comprises at least one of bone morphogenetic protein, bone ingrowth enhancing protein, or bone graft.

11. A device for distracting at least one pair of adjacent spinous processes, said device comprising:
    a main body including a shaft having a longitudinal axis;
    first and second hooks extending transversely from said main body, wherein at least one of said first and second hooks is slidably mounted with respect to said shaft;
    said hooks being integrally formed and rigid, with no moving parts, and configured and dimensioned to extend laterally from both lateral sides of the spinous processes when implanted therebetween and to be inserted between the spinous processes laterally from a single side thereof; and
    said hooks being variably positionable between a closed configuration, in which said hooks are positioned so as to be at least one of overlapping or in contact with one another, to facilitate insertion of said hooks between the adjacent spinous processes, and an open configuration, in which said hooks are separated from one another;

wherein said hooks slide past one another so as to be positioned at least partially side-by side when in said closed configuration; and wherein said hooks comprise beveled tips extending distally therefrom, wherein a main curvature of each said hook extends transversely from said longitudinal axis of said main body in a main direction of curvature, and wherein each of said beveled tips comprises a first side extending transversely relative to said longitudinal axis of said main body, in a direction away from said main direction of curvature of one of said first and second hooks from which it extends, and toward the other of said first and second hooks, and a second side substantially parallel with a second side of the other of said beveled tips.

12. The device of claim 1, wherein said arms comprise beveled tips extending distally therefrom.

13. The device of claim 12, wherein said first and second curvatures extend transversely from longitudinal axes of said first and second arms, respectively, and wherein each of said beveled tips extends transversely relative to said respective longitudinal axes of said first and second arms, in a direction away from said first and second curvatures, respectively.

14. An interspinous implant system for distracting and fusing at least one pair of adjacent spinous processes, said system comprising:

a device including:

a main body including a shaft having a longitudinal axis;

first and second hooks extending transversely from said main body, wherein one of said first and second hooks is slidably mounted with respect to said shaft and the other of said first and second hooks is rigidly and fixed mounted to said shaft;

said hooks being configured and dimensioned to extend laterally from both lateral sides of the spinous processes when implanted therebetween and to be inserted between the spinous processes laterally from a single side thereof;

said hooks being variably positionable between a closed configuration, in which said hooks are positioned so as to be at least one of overlapping or in contact with one another, to facilitate insertion of said hooks between the adjacent spinous processes, and an open configuration, in which said hooks are separated from one another, wherein at least a portion of said first hook is positioned below a corresponding portion of said second hook when said hooks are in said closed configuration, and said at least a portion of said first hook is positioned above said corresponding portion of said second hook when said hooks are in said open configuration; and a bone ingrowth enhancing agent;

wherein said hooks comprise beveled tips extending distally therefrom, wherein a main curvature of each said hook extends transversely from said longitudinal axis of said main body in a main direction of curvature, and wherein each of said beveled tips comprises a first side extending transversely relative to said longitudinal axis of said main body, in a direction away from said main direction of curvature of one of said first and second hooks from which it extends, and toward the other of said first and second hooks, and a second side substantially parallel with a second side of the other of said beveled tips.

15. The system of claim 14, wherein said hooks slide past one another so as to be positioned at least partially side-by side when in said closed configuration.

16. A kit for treatment of spinal disorders, said kit comprising:

a device including:

a main body including a shaft having a longitudinal axis;

first and second hooked arms extending transversely from said main body, wherein at least one of said first and second hooked arms is slidably mounted to said shaft to slide axially with respect to said shaft along a direction of said longitudinal axis;

said hooked arms being integrally formed and rigid, with no moving parts, and configured and dimensioned to extend laterally from both sides of spinous processes of adjacent vertebrae when implanted therebetween and to be inserted between the spinous processes laterally from a single side thereof;

said hooked arms being variably positionable between a closed configuration, in which said hooked arms at least partially overlap one another, to facilitate insertion of said hooked arms between the adjacent spinous processes, and an open configuration, in which said hooked arms are separated from one another and do not overlap; and a component for facilitating fusion of the adjacent vertebrae while said device is implanted between the spinous processes;

wherein said hooked arms comprise beveled tips extending distally therefrom, wherein a main curvature of each said hooked arm extends transversely from said longitudinal axis of said main body in a main direction of curvature, and wherein each of said beveled tips comprises a first side extending transversely relative to said longitudinal axis of said main body, in a direction away from said main direction of curvature of one of said first and second hooked arms from which it extends, and toward the other of said first and second hooked arms, and a second side substantially parallel with a second side of the other of said beveled tips.

17. The kit of claim 16, further comprising:

a tool for implanting said device.

18. The kit of claim 17, wherein said tool comprises:

a pair of distraction arms at a distal end portion of said tool pivotally mounted for movement towards and away from one another;

distal end portions of said distraction arms configured to slide over portions of the interspinous implant device to be implanted;

lock arms operable to lock said distal end portions to the interspinous implant device; and a pair of drive arms at a proximal end portion of said tool connected via the pivotal mount to said distraction arms and operable to drive said distraction arms toward each other and away from one another.

19. The kit of claim 16, further comprising a tool for delivering said component for facilitating fusion to a location of the adjacent spinous processes and said implant.

20. The system of claim 14, further comprising a bone ingrowth enhancing agent.

* * * * *